(12) United States Patent
Altmann et al.

(10) Patent No.: US 6,608,071 B2
(45) Date of Patent: Aug. 19, 2003

(54) ISOQUINOLINE DERIVATIVES WITH ANGIOGENESIS INHIBITING ACTIVITY

(75) Inventors: Karl-Heinz Altmann, Reinach (CH); Guido Bold, Gipf-Oberfrick (CH); Paul William Manley, Arlesheim (CH)

(73) Assignee: Novartis AG, Basel (CH)

( * ) Notice: Subject to any disclaimer, the term of this patent is extended or adjusted under 35 U.S.C. 154(b) by 140 days.

(21) Appl. No.: 09/781,036

(22) Filed: Feb. 9, 2001

(65) Prior Publication Data

US 2002/0010181 A1 Jan. 24, 2002

Related U.S. Application Data

(63) Continuation of application No. PCT/EP99/05781, filed on Aug. 9, 1999.

(30) Foreign Application Priority Data

Aug. 11, 1998 (CH) ............................................. 1654/98

(51) Int. Cl.$^7$ ...................... A61K 31/505; A61K 31/47; C07D 239/02; C07D 217/22
(52) U.S. Cl. ............. 514/269; 514/255.05; 514/252.04; 514/307; 514/309; 514/310; 544/238; 544/299; 544/326; 544/333; 546/141; 546/143; 546/148
(58) Field of Search ........................... 574/255.05, 269, 574/252.04, 307, 309, 310; 544/238, 299, 326, 333; 546/141, 143, 148

(56) References Cited

U.S. PATENT DOCUMENTS 4,943,581 A * 7/1990 Hidaka et al. .............. 514/307

FOREIGN PATENT DOCUMENTS

| WO | WO 97/30035 | 8/1997 |
| WO | WO 97/34876 | 9/1997 |
| WO | WO 98/35958 | 8/1998 |

\* cited by examiner

Primary Examiner—D. Margaret Seaman
(74) Attorney, Agent, or Firm—Joseph J. Borovian

(57) ABSTRACT

The invention relates to compounds of formula I

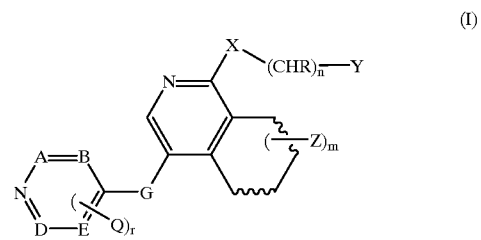

(I)

wherein
r is from 0 to 2; n is from 0 to 2; m is from 0 to 4;
A, B, D and E are each independently of the others N or CH, with the proviso that not more than two of those radicals are N;
G is lower alkylene, —CH$_2$—O—, —CH$_2$—S—, —CH$_2$—NH—, oxa (—O—), thia (—S—) or imino (—NH—), or is lower alkylene substituted by acyloxy or by hydroxy;
Q is lower alkyl, especially methyl;
R is H or lower alkyl;
X is imino, oxa or thia;
Y is lower alkyl or, especially, aryl, heteroaryl or unsubstituted or substituted cycloalkyl; and
Z is amino, mono- or di-substituted amino, halogen, alkyl, substituted alkyl, hydroxy, etherified or esterified hydroxy, nitro, cyano, carboxy, esterified carboxy, alkanoyl, carbamoyl, N-mono- or N,N-di-substituted carbamoyl, amidino, guanidino, mercapto, sulfo, phenylthio, phenyl-lower alkylthio, alkylphenylthio, phenylsulfinyl, phenyl-lower alkylsulfinyl, alkylphenyl-sulfinyl, phenylsulfonyl, phenyl-lower alkanesulfonyl or alkylphenylsulfonyl, and where, if more than one radical Z is present (m$\geq$2), the substituents Z are identical or different;
and wherein the bonds indicated by a wavy line are either single bonds or double bonds;
or an N-oxide of the mentioned compound, wherein one or more N atoms carry an oxygen atom;
or a salt thereof. The compounds inhibit especially angiogenesis.

12 Claims, No Drawings

ISOQUINOLINE DERIVATIVES WITH ANGIOGENESIS INHIBITING ACTIVITY

This is a continuation of International Application No. PCT/EP99/05781, filed Aug. 9, 1999, the contents of which are incorporated herein by reference.

The invention relates to novel isoquinoline derivatives, to a process for their preparation, to their use in a method of treating the human or animal body, to their use, alone or in combination with one or more other compounds having pharmaceutical activity, in the treatment of a disease (especially a proliferative disease), such as a tumour disease, to a method of treating such a disease in an animal, especially a human being, and to the use of such a compound, alone or in combination with one or more other compounds having pharmaceutical activity, in the preparation of a pharmaceutical composition (medicament) for the treatment especially of a proliferative disease, such as a tumour disease.

BACKGROUND TO THE INVENTION

Two processes, the de novo formation of vessels from differentiating endothelial cells or angioblasts in the developing embryo (vasculogenesis) and the budding of new capillary vessels from existing finished blood vessels (angiogenesis), are involved in the development of the vascular system of animal organs and tissues, as well as in transient phases of new vessel formation, for example in the female cycle, in pregnancy or in the healing of wounds. On the other hand, a number of diseases are known which are associated with deregulated angiogenesis, for example diseases caused by ocular neovascularisation, especially retinopathies (diabetic retinopathy, age-related macular degeneration); psoriasis; haemangioblastomas, such as "strawberry-marks" (=haemangioma); various inflammatory diseases, such as arthritis, especially rheumatoid arthritis, arterial atherosclerosis and atherosclerosis occurring after transplants, endometriosis or chronic asthma; and, especially, tumour diseases (solid tumours, but also leukaemias and other liquid tumours, since many primitive blood cells and leukaemia cells express c-kit, KDR and flt-1).

According to more recent experience, the angiogenic factor known as vascular endothelial growth factor=VEGF, and its cellular receptors, lies at the centre of the regulatory network which controls the growth and the differentiation of the blood vessel system and its parts, both during development of the embryo and during normal growth, and also in a large number of pathological abnormalities and diseases (see Breier, G., et al., Trends in Cell Biology 6, 454–456 (1996) and references cited therein).

VEGF is a dimeric, disulfide-linked 46 kDa glycoprotein and is related to platelet-derived growth factor (PDGF). It is secreted by normal cell lines and tumour cell lines, is an endothelial-cell-specific mitogen, has angiogenic activity in in vivo test systems (e.g. rabbit cornea), has chemotactic activity on endothelial cells and monocytes, and induces plasminogen activators in endothelial cells, which are then involved in the proteolytic degradation of the extracellular matrix during the budding of capillaries. A number of isoforms of VEGF are known, which have comparable biological activities but can be differentiated in respect of the secreting cell types and the heparin bond. In addition, there are other members of the VEGF family, for example placenta growth factor (PlGF) and VEGF-C.

VEGF receptors, by contrast, are transmembrane receptor tyrosine kinases and have an extracellular domain with seven immunoglobulin-like domains and an intracellular tyrosine kinase domain. Various types are known, for example VEGFR-1, VEGFR-2 and VEGFR-3.

A large number of human tumours express VEGF and bring about large-scale induction of its receptors, for example gliomas or carcinomas. This has led to the hypothesis that the VEGF released by tumour cells might stimulate the growth of blood capillaries and the proliferation of tumour endothelium in a paracrine manner and thus, as a result of the improved blood supply, might accelerate tumour growth. The occurrence of cerebral oedemas in glioma patients might also be explained by increased VEGF expression. Direct proof of the role of VEGF as a tumour angiogenesis factor in vivo has in fact been provided by studies in which VEGF expression or VEGF activity was inhibited. That was achieved by means of antibodies which inhibit VEGF activity, by means of dominant-negative VEGFR-2 mutants, which inhibited signal transmission, or by the use of antisense VEGF-RNA techniques. All methods of treatment led to reduced tumour growth of glioma cell lines or other tumour cell lines in vivo as a consequence of inhibited tumour angiogenesis.

Hypoxia, and also a large number of growth factors and cytokines, for example epidermal growth factor, transforming growth factor a, transforming growth factor β, interleukin 1 and interleukin 6, induce the expression of VEGF in cell tests. Angiogenesis is an essential prerequisite for tumours that grow beyond a maximum diameter of approximately from 1 to 2 mm, up to which size the supply of oxygen and nutrients to the tumour cells can still be effected by diffusion. Accordingly, above a certain size, every tumour, regardless of its origin and its cause, is dependent on angiogenesis for its growth.

Three principal mechanisms are of importance for the effectiveness of angiogenesis inhibitors against tumours: 1) inhibition of the growth of vessels, especially capillaries, into tumours having an avascular basis, so that, as a result of a balance between apoptosis and proliferation, no net tumour growth occurs; 2) prevention of the flushing out of metastasis-forming tumour cells as a consequence of a deficient blood supply to the tumours; and 3) inhibition of the growth of endothelial cells, which would normally line the vessels, with the absence of their paracrine growth-stimulating action on the surrounding tissue.

SUMMARY OF THE INVENTION

Surprisingly, it has now been found that isoquinoline derivatives of formula I shown below have advantageous pharmacological properties and, for example, inhibit the activity of VEGF receptor tyrosine kinase and VEGF-dependent cell proliferation. Details of further activities are described below.

The compounds of formula I permit, for example, an unexpected new method of treatment especially for diseases in the treatment of which, and also for the prophylaxis of which, inhibition of angiogenesis and/or of VEGF receptor tyrosine kinase exhibits advantageous effects.

3

Complete description of the invention

The invention relates to compounds of formula I

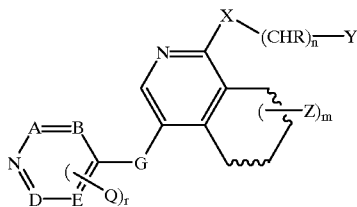

(I)

wherein
  r is from 0 to 2;
  n is from 0 to 2;
  m is from 0 to 4;
  A, B, D and E are each independently of the others N or CH, with the proviso that not more than two of those radicals are N;
  G is lower alkylene, —CH₂—O—, —CH₂—S—, —CH₂—NH—, oxa (—O—), thia (—S—) or imino (—NH—), or is lower alkylene substituted by acyloxy or by hydroxy;
  Q is lower alkyl, especially methyl;
  R is H or lower alkyl;
  X is imino, oxa or thia;
  Y is lower alkyl or, especially, aryl, heteroaryl or unsubstituted or substituted cycloalkyl; and
  Z is amino, mono- or di-substituted amino, halogen, alkyl, substituted alkyl, hydroxy, etherified or esterified hydroxy, nitro, cyano, carboxy, esterified carboxy, alkanoyl, carbamoyl, N-mono- or N,N-di-substituted carbamoyl, amidino, guanidino, mercapto, sulfo, phenylthio, phenyl-lower alkylthio, alkylphenylthio, phenylsulfinyl, phenyl-lower alkylsulfinyl, alkylphenylsulfinyl, phenylsulfonyl, phenyl-lower alkanesulfonyl or alkylphenylsulfonyl, and where, if more than one radical Z is present (m≧2), the substituents Z are identical or different;
and wherein the bonds indicated by a wavy line are either single bonds or double bonds;
or an N-oxide of the mentioned compound, wherein one or more N atoms carry an oxygen atom;
or a salt thereof.

Within the context of the present disclosure, the general terms used hereinbefore and hereinafter preferably have the following meanings, unless indicated otherwise:

The term "lower" denotes a radical having up to and including a maximum of 7, especially up to and including a maximum of 4, carbon atoms, the radicals in question being unbranched or branched one or more times.

Any reference to compounds, salts and the like in the plural is always to be understood as including one compound, one salt or the like.

Asymmetric carbon atoms which may be present (for example in compounds of formula I (or an N-oxide thereof) wherein n=1 and R is lower alkyl) may have the (R), (S) or (R,S) configuration, preferably the (R) or (S) configuration. Substituents at a double bond or a ring may be in the cis (=Z) or trans (=E) form. Accordingly, the present compounds may be in the form of isomeric mixtures or in the form of pure isomers, preferably in the form of an enantiomerically pure diastereoisomer.

4

The index r is preferably 0 or 1.

The index n is preferably 0 or 1, especially 0. It may also be 2.

The index m is preferably 0, 1 or 2, especially 0, or also 1.

Of the ring members A, B, D and E in formula I, not more than two are to be N, and the other two are CH. Preferably, the ring members A, B, D and E are each CH.

When G is a divalent group —CH₂—O—, —CH₂—S— or —CH₂—NH—, the methylene group is in each case bonded to the ring having the ring members A, B, D and E, while the hetero atom (O, S or NH) is bonded to the phthalazine ring in formula I.

Lower alkylene G may be branched or, preferably, unbranched and is especially branched or, preferably, unbranched $C_1$-$C_4$alkylene, especially methylene (—CH₂—), ethylene (—CH₂—CH₂—), trimethylene (—CH₂—CH₂—CH₂—) or tetramethylene (—CH₂—CH₂—CH₂—CH₂—). G is preferably methylene.

Acyl in acyloxy-substituted lower alkylene is preferably arylcarbonyloxy, wherein aryl is as defined below, especially benzoyloxy or lower alkanoyloxy, more especially benzoyloxy; acyloxy-substituted lower alkylene is especially benzoyloxy-substituted methylene.

Hydroxy-substituted lower alkylene is preferably hydroxymethylene (—CH(OH)—).

Either G as acyloxy- or hydroxy-substituted lower alkylene is preferred, or the other meanings of G mentioned hereinbefore and hereinafter are in each case especially preferred.

Q is preferably bonded to A or to D (r=1) or to both (r=2), so that A and/or D in the case where Q is bonded are C(—Q).

Lower alkyl is especially $C_1$-$C_4$alkyl, for example n-butyl, sec-butyl, tert-butyl, n-propyl, iso-propyl or, especially, methyl or also ethyl, or, in the case of Y as lower alkyl, it may be especially isopentyl.

Aryl is preferably an aromatic radical having from 6 to 14 carbon atoms, especially phenyl, naphthyl, fluorenyl or phenanthrenyl, the mentioned radicals being unsubstituted or substituted by one or more substituents, preferably up to three, especially one or two substituents, especially selected from amino, mono- or di-substituted amino, halogen, alkyl, substituted alkyl, hydroxy, etherified or esterified hydroxy, nitro, cyano, carboxy, esterified carboxy, alkanoyl, carbamoyl, N-mono- or N,N-di-substituted carbamoyl, amidino, guanidino, mercapto, sulfo, phenylthio, phenyl-lower alkylthio, alkylphenylthio, phenylsulfinyl, phenyl-lower alkylsulfinyl, alkylphenylsulfinyl, phenylsulfonyl, phenyl-lower alkanesulfonyl, alkylphenylsulfonyl, lower alkenyl, such as ethenyl, phenyl, lower alkylthio, such as methylthio, lower alkanoyl, such as acetyl, lower alkylmercapto, such as methylmercapto (—S—CH₃), halo-lower alkylmercapto, such as trifluoromethylmercapto (—S—CF₃), lower alkanesulfonyl, halo-lower alkanesulfonyl, such as, especially, trifluoromethanesulfonyl, dihydroxybora (—B(OH)₂), heterocyclyl, and lower alkylenedioxy, such as methylenedioxy, bonded to adjacent carbon atoms of the ring; aryl is preferably phenyl that is unsubstituted or substituted by one or two identical or different substituents from the group consisting of amino; lower alkanoylamino, especially acetylamino; halogen, especially fluorine, chlorine or bromine; lower alkyl, especially methyl, or also ethyl or propyl; halo-lower alkyl, especially trifluoromethyl; hydroxy; lower alkoxy, especially methoxy, or also ethoxy; phenyl-lower alkoxy, especially benzyloxy; and cyano, or (alternatively or additionally to the preceding group of substituents) $C_8$–$C_{12}$alkoxy, especially n-decyloxy, carbamoyl, lower alkylcarbamoyl, such as N-methyl- or N-tert-butyl-carbamoyl, lower alkanoyl, such as acetyl, phenyloxy, halo-lower alkyloxy, such as trifluoromethoxy or 1,1,2,2-tetrafluoroethyloxy, lower alkoxycarbonyl, such as ethoxycarbonyl, lower alkylmercapto, such as methylmercapto, halo-lower alkylmercapto, such as trifluoromethylmercapto, hydroxy-lower alkyl, such as hydroxymethyl or 1-hydroxymethyl, lower alkanesulfonyl, such as methanesulfonyl, halo-lower alkanesulfonyl, such as trifluoromethanesulfonyl, phenylsulfonyl, dihydroxybora (—B(OH)$_2$), 2-methyl-pyrimidin-4-yl, oxazol-5-yl, 2-methyl-1,3-dioxolan-2-yl, 1H-pyrazol-3-yl, 1-methyl-pyrazol-3-yl, and lower alkylenedioxy, such as methylenedioxy, bonded to two adjacent carbon atoms, more especially by one or two identical or different substituents selected from lower alkyl, especially methyl, halogen, especially chlorine or bromine, and halo-lower alkyl, especially trifluoromethyl. Aryl is preferably also naphthyl.

Heteroaryl is preferably an unsaturated heterocyclic radical in the bonding ring and is preferably mono- or also bi- or tri-cyclic; wherein at least in the ring bonding to the radical of the molecule of formula I one or more, preferably from one to four, especially one or two, carbon atoms of a corresponding aryl radical have been replaced by a hetero atom selected from the group consisting of nitrogen, oxygen and sulfur, the bonding ring having preferably from 4 to 12, especially from 5 to 7, ring atoms; wherein heteroaryl is unsubstituted or substituted by one or more, especially from one to three, identical or different substituents from the group consisting of the substituents mentioned above as substituents of aryl; and is especially a heteroaryl radical selected from the group consisting of imidazolyl, thienyl, furyl, pyranyl, thianthrenyl, isobenzofuranyl, benzofuranyl, chromenyl, 2H-pyrrolyl, pyrrolyl, lower alkyl-substituted imidazolyl, benzimidazolyl, pyrazolyl, thiazolyl, isothiazolyl, oxazolyl, isoxazolyl, pyridyl, pyrazinyl, pyrimidinyl, pyridazinyl, indolizinyl, isoindolyl, 3H-indolyl, indolyl, indazolyl, triazolyl, tetrazolyl, purinyl, 4H-quinolizinyl, isoquinolyl, quinolyl, phthalazinyl, naphthyridinyl, quinoxalyl, quinazolinyl, cinnolinyl, pteridinyl, carbazolyl, phenanthridinyl, acridinyl, perimidinyl, phenanthrolinyl and furazanyl, each of those radicals being bonded via a ring having at least one hetero atom to the radical of the molecule of formula I; pyridyl is especially preferred. Special preference is given also to indolyl that is substituted by halogen, especially by fluorine, especially 6-fluoroindol-3-yl.

Mono- or di-substituted amino is especially amino that is substituted by one or two identical or different radicals from lower alkyl, such as methyl; hydroxy-lower alkyl, such as 2-hydroxyethyl; phenyl-lower alkyl; lower alkanoyl, such as acetyl; benzoyl; substituted benzoyl, wherein the phenyl radical is unsubstituted or, especially, is substituted by one or more, preferably one or two, substituents selected from nitro and amino, or also from halogen, amino, N-lower alkylamino, N,N-di-lower alkylamino, hydroxy, cyano, carboxy, lower alkoxycarbonyl, lower alkanoyl and carbamoyl; and phenyl-lower alkoxycarbonyl wherein the phenyl radical is unsubstituted or, especially, is substituted by one or more, preferably one or two, substituents selected from nitro and amino, or also from halogen, amino, N-lower alkylamino, N,N-di-lower alkylamino, hydroxy, cyano, carboxy, lower alkoxycarbonyl, lower alkanoyl and carbamoyl; and is preferably N-lower alkylamino, such as N-methylamino, hydroxy-lower alkylamino, such as 2-hydroxyethylamino, phenyl-lower alkylamino, such as benzylamino, N,N-di-lower alkylamino, N-phenyl-lower alkyl-N-lower alkylamino, N,N-di-lower alkylphenylamino, lower alkanoylamino, such as acetylamino, or a substituent selected from the group consisting of benzoylamino and phenyl-lower alkoxycarbonylamino, wherein in each case the phenyl radical is unsubstituted or, especially, is substituted by nitro or amino, or also by halogen, amino, N-lower alkylamino, N,N-di-lower alkylamino, hydroxy, cyano, carboxy, lower alkoxycarbonyl, lower alkanoyl or by carbamoyl, or alternatively or additionally to the preceding group of radicals, by aminocarbonylamino.

Halogen is especially fluorine, chlorine, bromine or iodine, more especially fluorine, chlorine or bromine.

Alkyl has preferably up to a maximum of 12 carbon atoms and is especially lower alkyl, more especially methyl, or also ethyl, n-propyl, isopropyl or tert-butyl.

Substituted alkyl is alkyl as last defined, especially lower alkyl, preferably methyl, which may contain one or more, especially up to three, substituents selected especially from the group consisting of halogen, especially fluorine, and also amino, N-lower alkylamino, N,N-di-lower alkylamino, N-lower alkanoylamino, hydroxy, cyano, carboxy, lower alkoxycarbonyl and phenyl-lower alkoxycarbonyl. Trifluoromethyl is especially preferred.

Etherified hydroxy is especially $C_8$–$C_{20}$alkyloxy, such as n-decyloxy, lower alkoxy (preferred), such as methoxy, ethoxy, isopropyloxy or n-pentyloxy, phenyl-lower alkoxy, such as benzyloxy, or also phenyloxy, or, alternatively or additionally to the preceding group, $C_8$–$C_{20}$-alkyloxy, such as n-decyloxy, halo-lower alkoxy, such as trifluoromethyloxy or 1,1,2,2-tetrafluoroethoxy.

Esterified hydroxy is especially lower alkanoyloxy, benzoyloxy, lower alkoxycarbonyloxy, such as tert-butoxycarbonyloxy, or phenyl-lower alkoxycarbonyloxy, such as benzyloxy-carbonyloxy.

Esterified carboxy is especially lower alkoxycarbonyl, such as tert-butoxycarbonyl or ethoxy-carbonyl, phenyl-lower alkoxycarbonyl or phenyloxycarbonyl.

Alkanoyl is especially alkyl-carbonyl, more especially lower alkanoyl, for example acetyl.

N-Mono- or N,N-di-substituted carbamoyl is especially substituted at the terminal nitrogen by one or two substituents lower alkyl, phenyl-lower alkyl or hydroxy-lower alkyl.

Alkylphenylthio is especially lower alkylphenylthio.

Alkylphenylsulfinyl is especially lower alkylphenylsulfinyl.

Alkylphenylsulfonyl is especially lower alkylphenylsulfonyl.

Pyridyl Y is preferably 3- or 4-pyridyl.

Unsubstituted or substituted cycloalkyl is preferably $C_3$–$C_8$cycloalkyl which is unsubstituted or is substituted in the same manner as aryl, especially as defined for phenyl. Preference is given to cyclohexyl, or also cyclopentyl or cyclopropyl. Preference is given also to 4-lower alkyl-cyclohexyl, such as 4-tert-butylcyclohexyl.

Z is preferably amino, hydroxy-lower alkylamino, such as 2-hydroxyethylamino, lower alkanoylamino, such as acetylamino, nitrobenzoylamino, such as 3-nitrobenzoylamino, amino-benzoylamino, such as 4-aminobenzoylamino, phenyl-lower alkoxycarbonylamino, such as benzyloxycarbonylamino, or halogen, such as bromine; preferably only one substituent is present (m=1), especially one of the last-mentioned substituents, especially halogen. Very special preference is given to a compound of formula I (or an N-oxide thereof) wherein Z is not present (m=0).

Heterocyclyl is especially a five- or six-membered heterocycle having 1 or 2 hetero atoms selected from the group consisting of nitrogen, oxygen and sulfur, which heterocycle may be unsaturated or fully or partially saturated, and is unsubstituted or substituted, especially by lower alkyl, such as methyl; preference is given to a radical selected from 2-methyl-pyrimidin-4-yl, oxazol-5-yl, 2-methyl-1,3-dioxolan-2-yl, 1H-pyrazol-3-yl and 1-methyl-pyrazol-3-yl.

Aryl in the form of phenyl that is substituted by lower alkylenedioxy, such as methylene-dioxy, bonded to two adjacent carbon atoms is preferably 3,4-methylenedioxyphenyl.

The bonds in formula I indicated by wavy lines are either single or double bonds. Preferably they are both simultaneously either single or double bonds.

An N-oxide of a compound of formula I is preferably an N-oxide in which an isoquinoline ring nitrogen or a nitrogen in the ring having the ring members A, B, D and E carries an oxygen atom, or more than one of the mentioned nitrogen atoms carry an oxygen atom.

Salts are especially the pharmaceutically acceptable salts of compounds of formula I (or an N-oxide thereof).

Such salts are formed, for example, by compounds of formula I (or an N-oxide thereof) having a basic nitrogen atom as acid addition salts, preferably with organic or inorganic acids, especially the pharmaceutically acceptable salts. Suitable inorganic acids are, for example, hydrohalic acids, such as hydrochloric acid; sulfuric acid; or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, 2-hydroxybutyric acid, gluconic acid, glucosemonocarboxylic acid, fumaric acid, succinic acid, adipic acid, pimelic acid, suberic acid, azelaic acid, malic acid, tartaric acid, citric acid, glucaric acid, galactaric acid, amino acids, such as glutamic acid, aspartic acid, N-methylglycine, acetylaminoacetic acid, N-acetylasparagine, N-acetylcysteine, pyruvic acid, acetoacetic acid, phosphoserine, 2- or 3-glycerophosphoric acid, maleic acid, hydroxymaleic acid, methylmaleic acid, cyclohexanecarboxylic acid, benzoic acid, salicylic acid, 1- or 3-hydroxynaphthyl-2-carboxylic acid, 3,4,5-trimethoxybenzoic acid, 2-phenoxy-benzoic acid, 2-acetoxybenzoic acid, 4-aminosalicylic acid, phthalic acid, phenylacetic acid, glucuronic acid, galacturonic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalenedisulfonic acid, N-cyclohexylsulfamic acid, N-methyl-, N-ethyl- or N-propyl-sulfamic acid, or other organic protonic acids, such as ascorbic acid.

When negatively charged radicals, such as carboxy or sulfo, are present, salts with bases can also be formed, for example metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethylpiperidine or N,N'-dimethyl-piperazine.

When a basic group and an acid group are present in the same molecule, a compound of formula I (or an N-oxide thereof) can also form internal salts.

For isolation or purification it is also possible to use pharmaceutically unacceptable salts, for example picrates or perchlorates. Only the pharmaceutically acceptable salts or the free compounds (optionally in the form of pharmaceutical compositions) are used therapeutically, and those are therefore preferred.

In view of the close relationship between the novel compounds in free form and in the form of their salts, including also those salts which can be used as intermediates, for example in the purification of the novel compounds or for their identification, hereinbefore and hereinafter any reference to the free compounds is also to be understood as including the corresponding salts, as appropriate and expedient.

The compounds of formula I (or N-oxides thereof) have valuable pharmacological properties, as described at the beginning and hereinbelow.

The effectiveness of the compounds according to the invention as inhibitors of VEGF receptor tyrosine kinase activity can be demonstrated as follows:

Test for activity against VEGF receptor tyrosine kinase activity: The test is carried out using Flt-1 VEGF receptor tyrosine kinase. In detail, the procedure is as follows: 30 $\mu$l of kinase solution (10 ng of the kinase domain of Flt-1, Shibuya et al., Oncogene 5, 519–524 (1990)) in 20 mM Tris-HCl pH 7.6, 3 mM manganese dichloride ($MnCl_2$), 3 mM magnesium chloride ($MgCl_2$) and 3 $\mu$g/ml of poly(Glu, Tyr) 4:1 (Sigma, Buchs, Switzerland), 8 $\mu$M [$^{33}$P]-ATP (0.2 $\mu$Ci/batch), 1% dimethyl sulfoxide and from 0 to 50 $\mu$M of the test compound are incubated together for 15 minutes at room temperature. The reaction is then terminated by addition of 10 $\mu$l of 0.25M ethylenediamine tetraacetate (EDTA) pH 7. An aliquot of 20 $\mu$l is connected to a vacuum using a multichannel dispenser (LAB SYSTEMS, USA) on a PVDF (=polyvinyl difluoride) Immobilon P membrane (Millipore, USA), which is incorporated in a Millipore Microtiter filter manifold. When the liquid has been removed completely, the membrane is incubated 4 times in succession, in each case for 10 minutes, with shaking, in a washing bath containing 0.5% phosphoric acid ($H_3PO_4$), and is then mounted in a Hewlett Packard TopCount Manifold and, after addition of 10 $\mu$l of Microscint® ($\beta$-scintillation counter fluid; Packard, USA), the radioactivity is, measured. $IC_{50}$ values are determined by linear regression analysis of the percentage values for the inhibition of each compound at three concentrations (generally 0.01, 0.1 and 1 $\mu$M). The inhibition values ($IC_{50}$ with half-maximum inhibition as compared with a control without inhibitor of formula I) found are especially in the range of from 10 nmol/liter to 100 $\mu$mol/liter, more especially from 20 to 2000 nmol/liter.

By analogy, $IC_{50}$ inhibition values in the same range can be confirmed using KDR tyrosine receptor kinase.

The effectiveness of the compounds according to the invention against tumours can be demonstrated in vivo as follows:

In vivo effectiveness in the nude mouse xenotransplantate model: Female Balb/c nude mice (8–12 weeks old, e.g. Novartis Animal Farm, Sissein, Switzerland) are allowed free access to water and food, under sterile conditions. Tumours are induced in carrier mice by the subcutaneous injection of tumour cells (human epithelial tumour cell line A-431; American Type Culture Collection (ATCC), Rockville, Md., USA, Catalogue Number ATCC CRL 1555; cell line derived from an 85-year-old woman; epidermoid carcinoma cell line). The resulting tumours are in turn subjected to at least three transplantations before the beginning of the treatment. Tumour fragments (about 25 mg) are implanted subcutaneously into the left flank of the animals by means of a 13-gauge Trocar needle under Forene® anaesthesia (Abbott, Switzerland). Treatment with the respective test compound is begun as soon as the tumour has reached a mean tumour volume of 100 mm³. Tumour growth is measured two to three times weekly, in each case 24 hours after the last treatment, by measuring the length of two perpendicular axes. The tumour volumes are calculated by published methods (see Evans et al., Brit. J. Cancer 45, 466–468 (1982)). The effectiveness against tumours is calculated as the mean increase in tumour volume in the treated animals, divided by the mean increase in tumour volume in untreated animals (control), and, after multiplication by 100, is given as T/C %. Tumour regression (given in %) is given as the smallest mean tumour volume based on the mean tumour volume at the beginning of the treatment. The test compounds are administered daily by gavage.

Instead of tumour cell line A-431, other tumour cell lines may also be used analogously, for example the MCF-7 breast adenocarcinoma cell line (ATCC No. HTB 22; see also J. Natl. Cancer Inst. (Bethesda) 51, 1409–1416 (1973));

the MDA-MB 468 breast adenocarcinoma cell line (ATCC No. HTB 132; see also In Vitro 14, 911–915 (1978));

the MDA-MB 231 breast adenocarcinoma cell line (ATCC No. HTB 26; see also J. Natl. Cancer Inst. (Bethesda) 53, 661–674 (1974));

the Colo 205 colon carcinoma cell line (ATCC No. CCL 222; see also Cancer Res. 38, 1345–1355 (1978));

the HCT 116 colon carcinoma cell line (ATCC No. CCL 247); see also Cancer Res. 41, 1751–1756 (1981));

the DU145 prostate carcinoma cell line DU 145 (ATCC No. HTB 81; see also Cancer Res. 37, 4049–4058 (1978)); and the PC-3 prostate carcinoma cell line PC-3 (ATCC No. CRL 1435; see also Cancer Res. 40, 524–534 (1980)).

The inhibition of VEGF-induced KDR autophosphorylation can be verified by means of a further in vitro cell experiment: Transfixed CHO cells, which permanently express human VEGF receptor (KDR), are sown in culture medium (containing 10% foetal calf serum (=FCS)) in 6-well cell culture plates and are incubated at 37° C., 5% $CO_2$, until they are about 80% confluent. The test compounds are then diluted in culture medium (without FCS, with 0.1% bovine serum albumin=BSA) and, after removal of the FCS-containing medium, are added to the cells (controls receive medium without test compounds). After two hours' incubation at 37° C., recombinant VEGF is added thereto; the final concentration of VEGF is 20 ng/ml. After a further 5 minutes' incubation at 37° C., the cells are washed twice with ice-cold PBS (phosphate-buffered physiological saline) and immediately lysed in 100 μl of lysis buffer per well. After 15 minutes at 4° C. (on ice), the lysates are centrifuged in order to remove the cell nuclei, and the protein concentrations of the supernatants are determined by means of a commercial protein assay (BIORAD). The lysates can then either be used further immediately or, if required, stored at −20° C.

In order to determine KDR phosphorylation, a "sandwich ELISA" is carried out: A monoclonal antibody to KDR (for example Mab 1495.12.14; prepared by H. Towbin) is immobilised on black ELISA plates (OptiPlate™ HTRF-96 from Packard) (50 ng per well in 50 μl of PBS). The plates are then washed and any free protein binding sites that remain are saturated with 1% BSA in PBS. The cell lysates (20 μg of protein per well) are then incubated overnight at 4° C. together with an anti-phosphotyrosine antibody, which is coupled to alkaline phosphatase (PY20:AP from Transduction Laboratories). Binding of the anti-phosphotyrosine antibody is then demonstrated using a luminescent AP substrate (CDP-Star Ready to use with Emerald II; TROPIX). The luminescence is measured in a Packard Top Count Microplate Scintillation Counter (Top Count). The difference between the signal from the positive control (stimulated with VEGF) and that from the negative control (not stimulated with VEGF) corresponds to the VEGF-induced KDR phosphorylation (=100%). The activity of the substances tested is calculated as the % inhibition of VEGF-induced KDR phosphorylation, the concentration of a substance that brings about half-maximum inhibition being designated the ED50 (effective dose for 50% inhibition). Compounds of formula I exhibit ED50 values in the range of from 5 nM to 10 μM, especially from 5 nM to 500 nM.

The compounds of formula I, or their N-oxides, also inhibit to varying degrees other tyrosine kinases involved in signal transmission, which are mediated by trophic factors, for example abl kinase, kinases from the family of the src kinases, especially c-src kinase, lck, fyn; also kinases of the EGF family, for example c-erbB2 kinase (HER-2), c-erbB3 kinase, c-erbB4 kinase; the insulin-like growth factor receptor kinase (IGF-1 kinase), especially members of the PDGF receptor tyrosine kinase family, such as PDGF receptor kinase, CSF-1 receptor kinase, Kit receptor kinase and VEGF receptor kinase, especially KDR and Flk; and also serine/threonine kinases, which all play a role in growth regulation and transformation in mammalian cells, including human cells.

The inhibition of c-erbB2 tyrosine kinase (HER-2) can, for example, be measured analogously to that of EGF-R protein kinase (see House et al., Europ. J. Biochem. 140, 363–367 (1984)). C-erbB2 kinase can be isolated and its activity can be determined by processes known per se (see, for example, Akiyama et al, Science 232, 1644 (1986)).

The inhibiting action on PDGF receptor kinase can also be measured by the method described by Trinks et al. (see J. Med. Chem. 37(7): 1015–1027 (1994)).

On the basis of those tests, a compound of formula I according to the invention (or an N-oxide thereof) exhibits therapeutic activity especially against protein-kinase-dependent diseases, especially proliferative diseases.

On the basis of their efficacy as inhibitors of VEGF-receptor tyrosine kinase activity, the compounds of the formula I, especially the novel com-pounds of the formula IA invention, primarily inhibit the growth of blood vessels and are thus, for example, effec-tive against a number of diseases associated with deregulated angiogenesis, especially diseases caused by ocular neovascularisation, especially retinopathies, such as diabetic retinopathy or age-related macula degeneration, proliferative or exfoliative skin diseases, such as psoriasis; haemangioblastoma, such as "strawberry marks" (haemangioma); mes-angial cell proliferative disorders, such as chro-nic or acute inflammatory renal diseases, e.g. diabetic nephro-pathy, malignant nephrosclerosis, thrombotic microangiopathy syndro-mes or transplant rejection, or especially inflammatory renal disease, such as glomerulo-nephritis, especially mesangio-proliferative glomerulonephritis, haemolytic-uraemic syndrome, diabetic nephro-pathy, or hypertensive nephrosclerosis, atheroma, arterial reste-nosis, autoimmune diseases, acute inflammation, fibrotic disorders (e.g. hepatic cirrhosis), diabetes, endometriosis, chro-nic asthma, arterial or post-transplanta-tional atherosclerosis, neurodegenerative disorders and especially neoplastic diseases (solid tumours, but also leukemias and other "liquid tumours", especially those expressing c-kit, KDR or flt-1), such as especially breast cancer, cancer of the colon, lung cancer (especially small-cell lung cancer), or cancer of the prostate, Kaposi's sarcoma, CNS tumors, ovarian cancer, renal tumors or VHL tumors. A compound of formula I (or an N-oxide thereof) inhibits the growth of tumours and is especially suited to preventing the metastatic spread of tu-mours and the growth of micrometastases. Furthermore, they can be used in the treatment of inflammatory rheumatic or rheumatoid diseases and/or pain, more especially for the treatment of rheumatoid arthritis and/or pain.

The compounds of formula I in some cases also inhibit angiogenesis processes induced by other growth factors (for example PDGF or bFGF). Furthermore, they inhibit other kinases with varying degrees of potency, and can therefore be of use in controlling other syndromes.

A compound of formula I (or an N-oxide thereof) can be administered on its own or in combination with one or more other therapeutic agents, it being possible for fixed combinations to be used or for a compound according to the invention and one or more other therapeutic agents to be administered in a staggered manner over time or independently of one another, or the combined administration of fixed combinations and of one or more other therapeutic agents is possible. In particular, the administration of a compound of formula I (or an N-oxide thereof) for tumour treatment can be carried out, alongside or additionally, in combination with chemotherapy (combination with one or more other chemotherapeutic agents, especially cytostatics, or with hormones or compounds having a hormone-like activity), radiotherapy, immunotherapy, surgical treatment or combinations thereof. Long-term therapy is also possible, as is adjuvant therapy in conjunction with other treatment methods, such as those just mentioned. Treatment to maintain the status of a patient after tumour remission or even chemopreventive treatment, for example in the case of at-risk patients, is also possible.

There come into consideration as therapeutic agents with which the compounds according to the invention can be combined especially one or more antiproliferative, cytostatic or cytotoxic compounds, for example one or more chemotherapeutic agents selected from the group comprising an inhibitor of polyamine biosynthesis, an inhibitor of a protein kinase, especially of a serine/threonine protein kinase, such as protein kinase C, or of a tyrosine protein kinase, such as epidermal growth factor receptor protein tyrosine kinase, a cytokine, a negative growth regulator, such as TGF-β or IFN-β, an aromatase inhibitor, hormones or hormone analogues, and a conventional cytostatic agent.

Compounds according to the invention are intended not only for the (prophylactic and, preferably, therapeutic) treatment of human beings, but also for the treatment of other warm-blooded animals, for example of commercially useful animals, for example rodents, such as mice, rabbits or rats, or guinea pigs. They can also be used as standard compounds in the above-mentioned test systems, in order to permit comparison with other compounds.

In general, the invention relates also to the use of a compound of formula I (or an N-oxide thereof) in inhibiting VEGF-R tyrosine kinase activity.

A compound of formula I (or an N-oxide thereof) can also be used for diagnostic purposes, for example in order that tumours obtained from warm-blooded animals, especially human beings, as the original "host" and transplanted into mice, can be examined for reduced growth after addition of such a compound, in order thus to study their sensitivity to the compound in question, thus allowing possible methods of treatment for a tumour disease in the original host to be ascertained and determined better.

In the groups of preferred compounds of formula I mentioned below, definitions of substituents from the above-mentioned general definitions may expediently be used, for example in order to replace more general definitions by definitions that are more specific or, especially, by definitions that are indicated as being preferred; preference is in each case given to the definitions indicated above as being preferred or mentioned by way of example.

Preference is given to a compound of formula I wherein
r is from 0 to 2, preferably 0;
n is 0 or 1;
m is 1 or, especially, 0;
A, B, D and E are each CH, or A, D and E are each CH and B is N;
G is lower alkylene, especially methylene or ethylene (—CH$_2$—CH$_2$—), —CH$_2$—NH—, —CH$_2$—O—, hydroxymethylene or benzoyloxy-methylene;
Q is methyl which is bonded to A, to D or to A and D;
R is H or lower alkyl, especially H or methyl;
X is imino, oxa or thia;
Y is phenyl that is unsubstituted or substituted by one or two identical or different substituents selected from the group consisting of amino; lower alkanoylamino, especially acetylamino; halogen, especially fluorine, chlorine or bromine; lower alkyl, especially methyl, or also ethyl or propyl; halo-lower alkyl, especially trifluoromethyl; hydroxy; lower alkoxy, especially methoxy, or also ethoxy; phenyl-lower alkoxy, especially benzyloxy; and cyano, or (alternatively or additionally to the preceding group of substituents) lower alkenyl, such as ethenyl, $C_8$–$C_{12}$alkoxy, especially n-decyloxy, lower alkoxycarbonyl, such as tert-butoxy-carbonyl, carbamoyl, lower alkylcarbamoyl, such as N-methyl- or N-tert-butyl-carbamoyl, lower alkanoyl, such as acetyl, phenyloxy, halo-lower alkyloxy, such as trifluoromethoxy or 1,1,2,2-tetrafluoroethyloxy, lower alkoxycarbonyl, such as ethoxycarbonyl, lower alkylmercapto, such as methylmercapto, halo-lower alkylmercapto, such as trifluoromethylmercapto, hydroxy-lower alkyl, such as hydroxymethyl or 1-hydroxymethyl, lower alkanesulfonyl, such as methanesulfonyl, halo-lower alkanesulfonyl, such as trifluoromethanesulfonyl, phenylsulfonyl, dihydroxybora (—B(OH)$_2$), 2-methyl-pyrimidin-4-yl, oxazol-5-yl, 2-methyl-1,3-dioxolan-2-yl, 1H-pyrazol-3-yl, 1-methyl-pyrazol-3-yl, and lower alkylenedioxy, such as methylenedioxy, bonded to two adjacent carbon atoms, especially by one or two substituents selected from halogen, such as chlorine or bromine, lower alkyl, such as methyl, and halo-lower alkyl, such as trifluoromethyl; or Y is pyridyl, especially 3-pyridyl; Y is especially phenyl, 2-, 3- or 4-aminophenyl, 2-, 3- or 4-acetylaminophenyl, 2-, 3- or 4-fluorophenyl, 2-, 3- or 4-chlorophenyl, 2-, 3- or 4-bromophenyl, 2,3-, 2,4-, 2,5- or 3,4-dichlorophenyl, chloro-fluoro-phenyl, such as 3-chloro-4-fluoro-phenyl, or also 4-chloro-2-fluoroanilino, 2-, 3- or 4-methylphenyl, 2-, 3- or 4-ethylphenyl, 2-, 3- or 4-propylphenyl, methyl-fluoro-phenyl, such as 3-fluoro-4-methylphenyl, 2-, 3- or 4-trifluoromethylphenyl, 2-, 3- or 4-hydroxyphenyl, 2-, 3- or 4-methoxyphenyl, 2-, 3- or 4-ethoxyphenyl, methoxy-chloro-phenyl, such as 3-chloro-4-methoxycarbonyl, 2-, 3- or 4-benzyloxyphenyl, 2-, 3- or 4-cyanophenyl, or also 2-, 3- or 4-pyridyl; or Y is more especially 4-chlorophenyl, 2-, 3- or 4-methylphenyl, 4-chloro-5-trifluoromethylphenyl, 3-bromo-5-trifluoromethylphenyl, or Y is very especially 3,5-dimethylphenyl; or also is especially 4-methyl-3-iodophenyl, 3,4-bis(trifluoromethyl) phenyl, 3-bromo-4-ethyl-phenyl or 3-chlorobenzylphenyl;

Z is amino; N-lower alkylamino, such as N-methylamino; hydroxy-lower alkylamino, such as 2-hydroxyethylamino; phenyl-lower alkylamino, such as benzylamino; N,N-di-lower alkylamino; N-phenyl-lower alkyl-N-lower alkylamino; N,N-di-lower alkylphenylamino; lower alkanoylamino, such as acetylamino; or a substituent selected from the group consisting of benzoylamino and phenyl-lower alkoxycarbonylamino, wherein the phenyl radical in each case is unsubstituted or, especially, is substituted by nitro or by amino, or also by halogen, amino, N-lower alkylamino, N,N-di-lower alkylamino, hydroxy, cyano, carboxy, lower alkoxycarbonyl, lower alkanoyl or by carbamoyl; or Z is halogen, especially bromine; more especially amino, acetylamino, nitrobenzoylamino, aminobenzoylamino, 2-hydroxyethylamino, benzyloxycarbonylamino or bromine; and the bonds indicated by a wavy line are each a double bond, or also are each a single bond;

or a salt thereof.

Special preference is given to a compound of formula I wherein r is 0;

n is 0;

m is 0;

A, B, D and E are each CH;

G is lower alkylene, especially methylene;

X is imino;

Y is phenyl that is unsubstituted or substituted by one or two identical or different substituents selected from the group consisting of halogen, especially fluorine or, more especially, chlorine or bromine; lower alkyl, especially methyl; and halo-lower alkyl, especially trifluoromethyl; especially 4-chlorophenyl, 2-, 3- or 4-methylphenyl, 4-chloro-5-trifluoromethylphenyl, 3-bromo-5-trifluoromethylphenyl, or more especially 3,5-dimethylphenyl; or also 4-methyl-3-iodophenyl, 3,4-bis(trifluoromethyl)phenyl or 3-bromo-4-ethylphenyl; and the bonds indicated by a wavy line are double bonds;

or a salt thereof.

Special preference is given also to a compound of formula I wherein r is 0;

n is from 0 to 2;

m is 0;

A, B, D and E are each CH;

G is methylene;

R is H;

X is imino (NH); and

Y is phenyl that is unsubstituted or substituted by halogen, especially chlorine, or by lower alkoxy, especially methoxy, such as 4-chlorophenyl or 4-methoxyphenyl; naphthyl; cyclohexyl that is unsubstituted or substituted by lower alkyl, especially by tert-butyl, such as 4-tert-butyl-cyclohexyl; indolyl that is unsubstituted or substituted by halogen, especially by fluorine, especially 6-fluoroindol-3-yl; or lower alkyl, especially isopentyl;

or a salt thereof where a salt-forming group is present.

Special preference is given to a compound of formula I, especially of formula IA, as mentioned below in the Examples, especially in Examples 1 to 5, or a pharmaceutically acceptable salt thereof, especially to a compound mentioned specifically in the Examples or its salt.

Special preference is given also to all compounds of formula I having an IC$_{50}$ of less than 1 μM in Example 80.

Special preference is given also to a compound selected from the compounds mentioned in Examples 8, 17, 42, 45, 46, 47, 58, 60, 62, 68, 69, 70, 87, 100, 111, 112, 113, 115, 116, 117, 118 and 132, or a salt thereof.

Very special preference is given to the compound having the name N-(3,5-dimethyl-phenyl)-[4-(pyridin-4-ylmethyl)-isoquinolin-1-yl]amine (wherein, based on formula I, the symbols have the following meanings: r=n=m=0; A=B=D=E=CH; G=CH$_2$; X=NH; Y=3,5-dimethylphenyl); or a salt thereof.

The compounds according to the invention can be prepared by processes known per se for other compounds, especially by a) reacting a compound of formula II

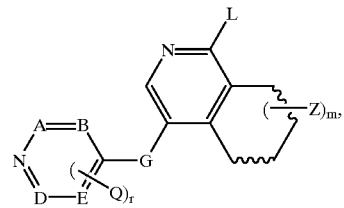

wherein r, m, A, B, D, E, G, Q and Z and the bonds indicated by wavy lines are as defined for a compound of formula I and L is a nucleofugal leaving group, with a compound of formula III

wherein n, R, X and Y are as defined for a compound of formula I, functional groups in the compounds of formula II and of formula III that are not to take part in the reaction being in protected form, if necessary, and removing any protecting groups that are present, wherein the starting compounds mentioned in process a) may also be in the form of salts where a salt-forming group is present and reaction in the salt form is possible;

and, if desired, converting a resulting compound of formula I, or an N-oxide thereof, into a different compound of formula I or an N-oxide thereof, converting a free compound of formula I, or an N-oxide thereof, into a salt, converting a resulting salt of a compound of formula I, or of an N-oxide thereof, into the free compound or into a different salt, and/or separating a mixture of isomeric compounds of formula I, or its N-oxide, into the individual isomers.

Detailed Description of the Process Variants:

In the following, more detailed description of the preparation process, r, n, m, A, B, D, E, G, Q, R, X, Y and Z and the bonds indicated by a wavy line are as defined for compounds of formula I, unless indicated otherwise.

Process a)

In the compound of formula II, a nucleofugal leaving group L is especially halogen, more especially bromine, iodine or, very especially, chlorine.

The reaction between the compound of formula II and the compound of formula III takes place in suitable inert polar solvents, especially alcohols, for example lower alkanols, such as methanol, propanol or, especially, ethanol or n-butanol, or it takes place in a melt without the addition of a solvent, especially when one of the reactants is in liquid form. The reaction takes place at elevated temperatures, preferably from approximately 60° C. to reflux temperature, for example under reflux conditions or at a temperature of from approximately 90 to approximately 110° C. The compound of formula III can also be used in the form of a salt, for example in the form of an acid addition salt with a strong acid, such as a hydrogen halide, for example in the form of the hydrochloride salt, or the corresponding acid, for example hydrochloric acid, can be added in a suitable solvent, for example an ether, such as dioxane.

Where one or more other functional groups, for example carboxy, hydroxy, amino or mercapto, in a compound of formula II and/or III are present in protected form or must be present in protected form because they are not to take part in the reaction, the protecting groups are groups which are customarily used in the synthesis of peptide compounds, but also in the synthesis of cephalosporins and penicillins as well as of nucleic acid derivatives and sugars. The protecting groups may already be present in the precursors and are to protect the functional groups in question against undesired secondary reactions, such as acylations, etherifications, esterifications, oxidations, solvolysis and the like. The protecting groups for functional groups in starting materials whose reaction is to be avoided, especially carboxy, amino, hydroxy and mercapto groups, include especially those protecting groups (conventional protecting groups) which are customarily used in the synthesis of peptide compounds, cephalosporins, penicillins or nucleic acid derivatives and sugars. The protecting groups may already be present in the precursors and are to protect the functional groups in question against undesired secondary reactions, such as acylations, etherifications, esterifications, oxidations, solvolysis, etc. In some cases the protecting groups can cause the reactions to proceed selectively, for example stereoselectively. It is a characteristic of protecting groups that they can be removed easily, that is to say without undesired secondary reactions, for example by solvolysis, by reduction, by photolysis or enzymatically, for example also under conditions analogous to physiological conditions, and that they are not present in the end products. The person skilled in the art will know or can readily find out which protecting groups are suitable in the reactions mentioned hereinbefore and hereinafter.

The protection of functional groups by means of such protecting groups, the protecting groups themselves, and reactions for their removal are described, for example, in standard works such as J. F. W. McOmie, "Protective Groups in Organic Chemistry", Plenum Press, London and New York 1973, in Th. W. Greene, "Protective Groups in Organic Synthesis", Wiley, New York 1981, in "The Peptides"; Volume 3 (E. Gross and J. Meienhofer, eds.), Academic Press, London and New York 1981, in "Methoden der organischen Chemie", Houben Weyl, 4th edition, Volume 15/I, Georg Thieme Verlag, Stuttgart 1974, in H.-D. Jakubke and H. Jescheit, "Aminosäuren, Peptide, Proteine", Verlag Chemie, Weinheim, Deerfield Beach and Basle 1982, and in Jochen Lehmann, "Chemie der Kohlenhydrate: Monosaccharide und Derivate", Georg Thieme Verlag, Stuttgart 1974.

Protecting groups mentioned in the Examples are preferably introduced and, if required, removed analogously to the mentioned methods.

Additional Process Steps

In the additional process steps, which are carried out if desired, functional groups in the starting compounds that are not to take part in the reaction may be present in unprotected form or in protected form, for example protected by one or more of the protecting groups mentioned above under process a). All or some of the protecting groups are then removed by one of the methods mentioned under process a).

Salts of compounds of formula I (or an N-oxide thereof) having a salt-forming group can be prepared in a manner known per se. For example, acid addition salts of compounds of formula I or their N-oxides can be obtained, for example, by treatment with an acid or a suitable anion exchange reagent. It is also possible to convert salts having two acid molecules (for example a dihalide of a compound of formula I (or of an N-oxide thereof)) into salts having one acid molecule per compound of formula I (or N-oxide thereof) (for example into a monohalide); that can be achieved, for example, by heating to the molten state or, for example, by heating in solid form under a high vacuum at elevated temperature, for example from 130 to 170° C., one molecule of the acid being expelled per molecule of a compound of formula I (or of an N-oxide thereof).

Salts can be converted into the free compounds in customary manner, for example by treatment with a suitable basic agent, for example with alkali metal carbonates, hydrogen carbonates or hydroxides, for example potassium carbonate or sodium hydroxide.

Stereoisomeric mixtures, for example mixtures of diastereoisomers, can be separated into the corresponding isomers in a manner known per se by means of suitable separating procedures. For example, diastereoisomeric mixtures can be separated into the individual diastereoisomers by fractional crystallisation, chromatography, solvent partitioning and the like. The separation may be carried out either at the stage of one of the starting materials or in the case of the compounds of formula I themselves. Enantiomers can be separated by formation of diastereoisomeric salts, for example by salt formation with an enantiomerically pure chiral acid, or by chromatographic methods, for example by chromatography, e.g. HPLC, on chromatographic carrier materials with chiral ligands.

A compound of formula I can be converted into a corresponding N-oxide. The reaction is carried out with a suitable oxidising agent, preferably a peroxide, for example m-chloroperbenzoic acid, in a suitable solvent, for example a halogenated hydrocarbon, such as chloroform or methylene chloride, or in a lower alkanecarboxylic acid, such as acetic acid, preferably at a temperature of from 0° C. to the boiling temperature of the reaction mixture, especially approximately room temperature.

A compound of formula I (or an N-oxide thereof) wherein Z is lower alkanoylamino can be hydrolysed to the corresponding amino compound (Z=amino), for example by hydrolysis with an inorganic acid, especially hydrochloric acid (HCl), in aqueous solution, it being possible to add further solvents, preferably at elevated temperature, for example under reflux.

A compound of formula I (or an N-oxide thereof) wherein Z is amino substituted by one or two identical or different radicals selected from lower alkyl, hydroxy-lower alkyl and phenyl-lower alkyl can be converted into the compound that is correspondingly substituted at the amino group, for example, by reaction with a lower alkyl halide, a hydroxy-lower alkyl halide, which is hydroxy-protected if necessary (see process a)), or a phenyl-lower alkyl halide under reaction conditions analogous to those mentioned under process a). For the introduction of 2-hydroxy-lower alkyl substituents at the amino group Z, addition starting from an epoxide (for example ethylene oxide) is also possible. The addition is carried out especially in aqueous solution and/or in the presence of polar solvents, such as alcohols, for example methanol, ethanol, isopropanol or ethylene glycol, ethers, such as dioxane, amides, such as dimethyl formamide, or phenols, such as phenol, also under anhydrous conditions, in apolar solvents, such as benzene and toluene, or in benzene/water emulsions, optionally in the presence of acid or basic catalysts, for example of alkaline solutions, such as sodium hydroxide solution, or in the presence of hydrazine-doped solid phase catalysts, such as aluminium oxide, in ethers, for example diethyl ether, generally at temperatures of approximately from 0° C. to the boiling temperature of the reaction mixture in question, preferably at from 20° C. to reflux temperature, where appropriate under elevated pressure, for example in a bomb tube, whereby the boiling temperature may also be exceeded, and/or under an inert gas, such as nitrogen or argon. Reductive alkylation of an amino group Z with a lower alkanealdehyde, a phenyl-lower alkanealdehyde or a hydroxy-lower alkanealdehyde, which is hydroxy-protected if necessary, is also possible. The reductive alkylation preferably takes place with hydrogenation in the presence of a catalyst, especially a noble metal catalyst, such as platinum or, especially, palladium, which is preferably bonded to a support material, such as carbon, or a heavy metal catalyst, such as Raney nickel, at normal pressure or at pressures of from 0.1 to 10 megapascals (MPa), or with reduction by means of complex hydrides, such as boron hydrides, especially alkali metal cyanoborohydrides, for example sodium cyanoborohydride, in the presence of a suitable acid, preferably of a relatively weak acid, such as a lower alkanecarboxylic acid or, especially, a sulfonic acid, such as p-toluenesulfonic acid; in customary solvents, for example alcohols, such as methanol or ethanol, or ethers, for example cyclic ethers, such as tetrahydrofuran, in the absence or presence of water.

In a compound of formula I (or an N-oxide thereof), an amino group Z can be converted by acylation into an amino group that is substituted by lower alkanoyl, benzoyl, substituted benzoyl or by phenyl-lower alkoxycarbonyl wherein the phenyl radical is unsubstituted or substituted. The corresponding acids contain a free carboxy group or are in the form of reactive acid derivatives thereof, for example in the form of the derived activated esters or reactive anhydrides, also reactive cyclic amides. The reactive acid derivatives can also be formed in situ. Activated esters are especially esters that are unsaturated at the linking carbon atom of the radical to be esterified, for example of the vinyl ester type, such as vinyl esters (obtainable, for example, by transesterification of a corresponding ester by vinyl acetate; activated vinyl ester method), carbamoyl esters (obtainable, for example, by treating the corresponding acid with an isoxazolium reagent; 1,2-oxazolium or Woodward method), or 1-lower alkoxyvinyl esters (obtainable, for example, by treating the corresponding acid with a lower alkoxyacetylene; ethoxyacetylene method), or esters of the amidino type, such as N,N'-disubstituted amidino esters (obtainable, for example, by treating the corresponding acid with a suitable N,N'-disubstituted carbodiimide, for example N,N'-dicyclohexylcarbodiimide or, especially, N-(3-dimethylaminopropyl)-N'-ethylcarbodiimide; carbodiimide method) or N,N-disubstituted amidino esters (obtainable, for example, by treating the corresponding acid with an N,N-disubstituted cyanamide; cyanamide method), suitable aryl esters, especially phenyl esters suitably substituted by electrophilic substituents (obtainable, for example, by treating the corresponding acid with a suitably substituted phenol, for example 4-nitrophenol, 4-methylsulfonylphenol, 2,4,5-trichlorophenol, 2,3,4,5,6-pentachlorophenol or 4-phenyldiazophenol, in the presence of a condensing agent, such as N,N'-dicyclohexyl-carbodiimide; activated aryl esters method), cyanomethyl esters (obtainable, for example, by treating the corresponding acid with chloroacetonitrile in the presence of a base; cyano-methyl esters method), thioesters, especially unsubstituted or substituted, for example nitro-substituted, phenylthio esters (obtainable, for example, by treating the corresponding acid with unsubstituted or substituted, for example nitro-substituted, thiophenols, inter alia by means of the anhydride or carbodiimide method; activated thiolesters method), or, especially, amino or amido esters (obtainable, for example, by treating the corresponding acid with an N-hydroxyamino or N-hydroxyamido compound, for example N-hydroxysuccinimide, N-hydroxypiperidine, N-hydroxyphthalimide, N-hydroxy-5-norbornene-2,3-dicarboxylic acid imide, 1-hydroxybenztriazole or 3-hydroxy-3,4-dihydro-1,2,3-benztriazin-4-one, for example by the anhydride or carbodiimide method; activated N-hydroxy esters method). Internal esters, for example γ-lactones, can also be used. Anhydrides of acids may be symmetrical or, preferably, mixed anhydrides of those acids, for example anhydrides with inorganic acids, such as acid halides, especially acid chlorides (obtainable, for example, by treating the corresponding acid with thionyl chloride, phosphorus pentachloride, phosgene or oxalyl chloride; acid chloride method), azides (obtainable, for example, from a corresponding acid ester via the corresponding hydrazide and treatment thereof with nitrous acid; azide method), anhydrides with carbonic acid semiesters, for example carbonic acid lower alkyl semiesters (especially chloroformic acid methyl esters) (obtainable, for example, by treating the corresponding acid with chloroformic acid lower alkyl esters or with a 1-lower alkoxycarbonyl-2-lower alkoxy-1,2-dihydroquinoline; mixed O-alkylcarbonic acid anhydrides method), or anhydrides with dihalogenated, especially dichlorinated, phosphoric acid (obtainable, for example, by treating the corresponding acid with phosphorus oxychloride; phosphorus oxychloride method), anhydrides with other phosphoric acid derivatives (for example those which can be obtained with phenyl N-phenylphosphoramidochloridate, or by reacting alkylphosphoric acid amides in the presence of sulfonic acid anhydrides and/or racemisation-reducing additives, such as N-hydroxybenzotriazole, or in the presence of cyanophosphonic acid diethyl ester) or with phosphorous acid derivatives, or anhydrides with organic acids, such as mixed anhydrides with organic carboxylic acids (obtainable, for example, by treating the corresponding acid with an unsubstituted or substituted lower alkane- or phenyl-lower alkane-carboxylic acid halide, for example phenylacetic acid, pivalic acid or trifluoroacetic acid chloride; mixed carboxylic acid anhydrides method) or with organic sulfonic acids (obtainable, for example, by treating a salt, such as an alkali metal salt, of the corresponding acid with a suitable organic sulfonic acid halide, such as lower alkane- or aryl-, for example methane- or p-toluene-sulfonic acid chloride; mixed sulfonic acid anhydrides method) as well as symmetrical anhydrides (obtainable, for example, by condensing the corresponding acid in the presence of a carbodiimide or of 1-diethylaminopropyne; symmetrical anhydrides method). Suitable cyclic amides are especially amides with five-membered diazacycles of aromatic nature, such as amides with imidazoles, for example imidazole (obtainable, for example, by treating the corresponding acid with N,N'- carbonyldiimidazole; imidazole method), or pyrazole, for example 3,5-dimethylpyrazole (obtainable, for example, via the acid hydrazide by treatment with acetylacetone; pyrazolide method). As mentioned, derivatives of carboxylic acids which are used as acylating agents can also be formed in situ. For example, N,N'-disubstituted amidino esters can be formed in situ by reacting the mixture of the starting material of formula I and the acid used as acylating agent in the presence of a suitable N,N'-disubstituted carbodiimide, for example N,N'-dicyclohexylcarbodiimide or, especially, N-(3-dimethylaminopropyl)-N'-ethylcarbodiimide. Furthermore, amino or amido esters of the acids used as acylating agent can be formed in the presence of the starting material of formula I to be acylated, by reacting a mixture of the corresponding acid and amino starting materials in the presence of an N,N'-disubstituted carbodiimide, for example N,N'-dicyclohexylcarbodiimide, and of an N-hydroxyamine or N-hydroxyamide, for example N-hydroxysuccinimide, optionally in the presence of a suitable base, for example 4-dimethylaminopyridine. Moreover, activation can be achieved in situ by reaction with N,N,N',N'-tetraalkyluronium compounds, such as O-benztriazol-1-yl-N,N,N',N'-tetra-methyl-uronium hexafluorophosphate, O-(1,2-dihydro-2-oxo-1-pyridyl)-N,N,N',N'-tetramethyluronium tetrafluoroborate (in the absence or presence of 1,8-diazabicyclo[5.4.0]undec-7-ene-(1,5,5)) or O-(3,4-dihydro-4-oxo-1,2,3-benztriazolin-3-yl)-N,N,N',N'-tetramethyluronium tetrafluoroborate. Finally, phosphoric acid anhydrides of the carboxylic acids can be prepared in situ by reacting an alkylphosphoric acid amide, such as hexamethylphosphoric acid triamide, in the presence of a sulfonic acid anhydride, such as 4-toluenesulfonic acid anhydride, with a salt, such as a tetrafluoroborate, for example sodium tetrafluoroborate, or with a different derivative of hexamethylphosphoric acid triamide, such as benzotriazol-1-yl-oxytris(dimethylamino)phosphonium hexafluoride, preferably in the presence of a racemisation-reducing additive, such as N-hydroxybenztriazole. If desired, an organic base is added, preferably a tertiary amine, for example a tri-lower alkylamine, especially ethyldiisopropylamine or, more especially, triethylamine, and/or a heterocyclic base, for example 4-dimethylaminopyridine or, preferably, N-methylmorpholine or pyridine. The condensation is preferably carried out in an inert, aprotic, preferably anhydrous solvent or solvent mixture, for example in a carboxylic acid amide, for example formamide or dimethylformamide, a halogenated hydrocarbon, for example methylene chloride, carbon tetrachloride or chloro-benzene, a ketone, for example acetone, a cyclic ether, for example tetrahydrofuran or dioxane, an ester, for example ethyl acetate, or a nitrile, for example acetonitrile, or in a mixture thereof, where appropriate at reduced or elevated temperature, for example in a temperature range of from approximately $-40°$ C. to approximately $+100°$ C., preferably from approximately $-10°$ C. to approximately $+70°$ C., where arylsulfonyl esters are used also at approximately from $+100°$ C. to $+200°$ C., especially at temperatures of from 10 to 30° C., and, where appropriate, under an inert gas atmosphere, for example a nitrogen or argon atmosphere. Aqueous, for example alcoholic, solvents, e.g. ethanol, or aromatic solvents, e.g. benzene or toluene, are also possible.

A nitro group Z in a compound of formula I can be reduced to an amino group, for example by reduction with metals or selective hydrogenation; for example by reaction with magnesium/ammonium sulfate in a water/alcohol mixture, such as methanol/water, at elevated temperature, for example from 30 to 60° C. (see Synth. Commun. 25(2), 4025–4028 (1995)); by reaction with zinciborohydride in an acid amide, such as dimethylformamide, at temperatures below room temperature, for example at approximately 0° C.; by reaction with 1,1'-di-octyl-4,4'-bipyridinium dibromide/sodium tetrathionate/potassium carbonate in water/halogenated hydrocarbon mixtures, for example water/methylene chloride mixtures, at elevated temperature, for example from 25 to 35° C. (see Tetrahedron Lett. 34(46), 7445–7446 (1993)); with sodium borohydride on Amberlyte IRA-400 ion exchanger in the chloride form in an alcohol, such as methanol/water, at preferred temperatures of from 0 to 40° C. (see Synthetic Commun. 19(5/6), 805–811 (1989)); with potassium borohydride in a halogenated hydrocarbon/alcohol mixture, for example methylene chloride/methanol, at preferred temperatures of from 10 to 35° C. (see Synthetic Commun. 9(1 7), 3047–3050 (1989)); with sodium borohydride in dioxane; with borane in tetrahydrofuran; by hydrogenation in the presence of Pd/C in an alcohol at a preferred temperature of from 0 to 35° C. and in the presence of ammonium formate (see Tetrahedron Lett. 25(32), 3415–3418 (1989)); with titanium tetrachloride/lithium aluminium hydride or titanium tetrachloride/magnesium in an ether, such as tetrahydrofuran (see Bull. Chem. Soc. Belg. 97(1), 51–53 (1988)); or with ferric ammonium chloride/water at elevated temperature, preferably under reflux (Synth. Commun. 22, 3189–3195 (1992)).

In a compound of formula I wherein G is acyloxy-substituted lower alkyl and the other radicals are as defined for formula I, the acyl radical can be removed by hydrolysis, yielding the corresponding compound of formula I wherein G is hydroxy-substituted lower alkylene. The hydrolysis is preferably carried out under customary conditions, for example in the presence of acids or bases, such as HCl or NaOH, in aqueous solution or in a suitable solvent or solvent mixture.

From a compound of formula I wherein G is acyloxy-substituted lower alkyl it is also possible to prepare a compound of formula I wherein G is lower alkylene. The reaction in that case is preferably carried out with catalytic hydrogenation (hydrogen in the presence of a suitable catalyst) in a customary solvent or solvent mixture.

General Process Conditions

All the process steps mentioned in the present text can be carried out under reaction conditions which are known per se, preferably those mentioned specifically, in the absence or, customarily, in the presence of solvents or diluents, preferably those which are inert towards the reagents used and are solvents therefor, in the absence or presence of catalysts, condensing agents or neutralising agents, for example ion exchangers, such as cation exchangers, for example in the $H^+$ form, depending on the nature of the reaction and/or of the reactants at reduced, normal or elevated temperature, for example in a temperature range of from approximately $-100°$ C. to approximately $190°$ C., preferably from approximately $-80°$ C. to approximately $150°$ C., for example at from $-80$ to $-60°$ C., at room temperature, at from $-20$ to $40°$ C. or at the boiling point of the solvent used, under atmospheric pressure or in a closed vessel, where appropriate under pressure, and/or in an inert atmosphere, for example under an argon or nitrogen atmosphere.

In all starting materials and intermediate compounds, salts can be present where salt-forming groups are present. Salts can also be present during the reaction of such compounds, provided that the reaction is not impaired thereby.

At all stages of the reaction, isomeric mixtures that form can be separated into the individual isomers, for example diastereoisomers or enantiomers, or into any desired mixtures of isomers, for example racemates or diastereoisomeric mixtures, for example analogously to the methods described under "Additional process steps".

In certain cases, for example in the case of hydrogenations, it is possible to achieve stereoselective reactions so that, for example, it is easier to obtain individual isomers.

The solvents from which those that are suitable for a particular reaction can be selected include, for example, water, esters, such as lower alkyl lower alkanoates, for example diethyl acetate, ethers, such as aliphatic ethers, for example diethyl ether, or cyclic ethers, for example tetrahydrofuran, liquid aromatic hydrocarbons, such as benzene or toluene, alcohols, such as methanol, ethanol or 1- or 2-propanol, nitriles, such as acetonitrile, halogenated hydrocarbons, such as methylene chloride, acid amides, such as dimethylformamide, bases, such as heterocyclic nitrogen bases, for example pyridine, carboxylic acids, such as lower alkanecarboxylic acids, for example acetic acid, carboxylic acid anhydrides, such as lower alkanoic acid anhydrides, for example acetic anhydride, cyclic, linear or branched hydrocarbons, such as cyclohexane, hexane or isopentane, or mixtures of those solvents, for example aqueous solutions, unless indicated otherwise in the description of the processes. Such solvent mixtures can also be used in working up, for example by chromatography or partitioning.

The invention relates also to those forms of the process in which a compound obtainable as an intermediate at any stage is used as starting material and the remaining steps are carried out, or the process is interrupted at any stage, or a starting material is formed under the reaction conditions or is used in the form of a reactive derivative or salt, or a compound obtainable by the process according to the invention is produced under the process conditions and is processed further in situ. There are preferably used those starting materials which lead to the compounds described above as being preferred, especially as being especially preferred, more especially preferred and/or very especially preferred.

The preparation of compounds of formula I (or N-oxides thereof) is preferably carried out analogously to the processes and process steps mentioned in the Examples.

The compounds of formula I (or N-oxides thereof), including their salts, can also be obtained in the form of hydrates, or their crystals can include, for example, the solvent used for crystallisation (presence in the form of solvates).

Pharmaceutical Compositions, Methods and Uses

The present invention relates also to pharmaceutical compositions which comprise a compound of formula I (or an N-oxide thereof) as active ingredient and can be used especially in the treatment of the diseases mentioned at the beginning. Special preference is given to compositions for enteral, such as nasal, buccal, rectal or, especially, oral, and parenteral, such as intravenous, intramuscular or subcutaneous, administration to warm-blooded animals, especially human beings. The compositions comprise the active ingredient on its own or, preferably, together with a pharmaceutically acceptable carrier. The dose of active ingredient depends on the disease to be treated and on the species, its age, weight and individual condition, individual pharmacokinetic data and on the mode of administration.

The invention relates also to pharmaceutical compositions for use in a method of treating the human or animal body prophylactically or, especially, therapeutically, to a process for their preparation (especially in the form of compositions for the treatment of tumours) and to a method of treating the above-mentioned diseases, especially tumour diseases, more especially those mentioned above.

The invention relates also to processes, and to the use of compounds of formula I (or an N-oxide thereof), for the preparation of pharmaceutical compositions comprising compounds of formula I (or an N-oxide thereof) as active component (active ingredient).

Preference is given to a pharmaceutical composition which is suitable for administration to a warm-blooded animal, especially a human being or a commercially useful mammal, which is suffering from a disease responsive to inhibition of angiogenesis or of VEGF receptor tyrosine kinase, for example psoriasis or, especially, a tumour disease, comprising a compound of formula I (or an N-oxide thereof), or a pharmaceutically acceptable salt thereof where salt-forming groups are present, in an amount that is effective in inhibiting angiogenesis or VEGF receptor tyrosine kinase, together with at least one pharmaceutically acceptable carrier.

Preference is given also to a pharmaceutical composition for the prophylactic or, especially, therapeutic treatment of tumour diseases and other proliferative diseases in a warm-blooded animal, especially a human being or a commercially useful mammal, which requires such treatment, especially which is suffering from such a disease, comprising a novel compound of formula I (or an N-oxide thereof), or a pharmaceutically acceptable salt thereof, as active ingredient in an amount that is effective prophylactically or, especially, therapeutically against the mentioned diseases.

Pharmaceutical compositions comprise from approximately 1% to approximately 95% active ingredient, dosage forms that are in single dose form preferably comprising from approximately 20% to approximately 90% active ingredient, and dosage forms that are not in single dose form preferably comprising from approximately 5% to approximately 20% active ingredient. Unit dose forms are, for example, dragées, tablets, ampoules, vials, suppositories or capsules. Other dosage forms are, for example, ointments, creams, pastes, foams, tinctures, lipsticks, drops, sprays, dispersions, etc. Examples are capsules comprising from approximately 0.05 g to approximately 1.0 g of the active ingredient.

The pharmaceutical compositions of the present invention are prepared in a manner known per se, for example by means of conventional mixing, granulating, confectioning, dissolving or lyophilising processes.

Solutions of the active ingredient are preferably used, in addition also suspensions or dispersions, especially isotonic aqueous solutions, dispersions or suspensions, which, in the case of, for example, lyophilised compositions which contain the active substance alone or together with a carrier, for example mannitol, can be prepared prior to use. The pharmaceutical compositions may be sterilised and/or comprise excipients, for example preservatives, stabilisers, wetting agents and/or emulsifiers, solubilisers, salts for regulating the osmotic pressure and/or buffers, and are prepared in a manner known per se, for example by means of conventional dissolving or lyophilising processes. The mentioned solutions or suspensions may comprise viscosity-increasing substances, such as sodium carboxy-methylcellulose, carboxymethylcellulose, dextran, polyvinylpyrrolidone or gelatin, or solubilisers, for example Tween 80 [polyoxyethylene(20)sorbitan monooleate; trade mark of ICI Americas, Inc, USA].

Suspensions in oil comprise as the oily component the vegetable, synthetic or semi-synthetic oils customary for injection purposes. There may be mentioned as such especially liquid fatty acid esters, which comprise as the acid component a long-chained fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid or linoleic acid, optionally with the addition of anti-oxidants, for example vitamin E, β-carotene or 3,5-di-tert-butyl-4-hydroxytoluene. The alcohol component of those fatty acid esters has a maximum of 6 carbon atoms and is a mono- or poly-hydric, for example mono-, di- or tri-hydric, alcohol, for example methanol, ethanol, propanol, butanol or pentanol or their isomers, but especially glycol and glycerol. Examples of fatty acid esters which may be mentioned are, therefore: ethyl oleate, isopropyl myristate, isopropyl palmitate, "Labrafil M 2375" (polyoxyethyleneglycerol trioleate from Gattefosse, Paris), "Labrafil M 1944 CS" (unsaturated polyglycolised glycerides prepared by alcoholysis of apricot kernel oil and composed of glycerides and polyethylene glycol ester; Gattefosse, France), "Labrasol" (saturated polyglycolised glycerides prepared by alcoholysis of TCM and composed of glycerides and polyethylene glycol ester; Gattefosse, France) and/or "Miglyol 812" (triglyceride of saturated fatty acids having a chain length of from $C_8$ to $C_{12}$ from Hüls AG, Germany), but especially vegetable oils, such as cottonseed oil, almond oil, olive oil, castor oil, sesame oil, soybean oil and, more especially, groundnut oil.

The preparation of the injection compositions is carried out in customary manner under sterile conditions, as are also the introduction thereof, for example, into ampoules or vials and the sealing of the containers.

Pharmaceutical compositions for oral administration can be obtained, for example, by combining the active ingredient with one or more solid carriers, granulating a resulting mixture, where appropriate, and processing the mixture or granules, if desired, where appropriate by addition of additional excipients, to tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, also binders, such as starches, for example corn, wheat, rice or potato starch, methylcellulose, hydroxypropylmethylcellulose, sodium carboxymethylcellulose and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Dragée cores can be provided with suitable, optionally enteric, coatings, there being used inter alia concentrated sugar solutions which may contain gum arabic, talc, polyvinylpyrrolidone, polyethylene glycol and/or titanium dioxide, or coating solutions in suitable organic solvents or solvent mixtures or, for the preparation of enteric coatings, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Pharmaceutical compositions for oral administration are also hard gelatin capsules and soft sealed capsules consisting of gelatin and a plasticiser, such as glycerol or sorbitol. The hard gelatin capsules may contain the active ingredient in the form of granules, for example in admixture with fillers, such as corn starch, binders and/or glidants, such as talc or magnesium stearate, and optionally stabilisers. In soft capsules the active ingredient is preferably dissolved or suspended in suitable liquid excipients, such as fatty oils, paraffin oil or liquid polyethylene glycols or fatty acid esters of ethylene glycol or propylene glycol, it likewise being possible to add stabilisers and detergents, for example of the polyoxyethylene-sorbitan fatty acid ester type.

Suitable rectally administrable pharmaceutical compositions are, for example, suppositories that consist of a combination of the active ingredient with a suppository base. Suitable suppository bases are, for example, natural or synthetic triglycerides, paraffin hydrocarbons, polyethylene glycols or higher alkanols.

For parenteral administration there are suitable, especially, aqueous solutions of an active ingredient in water-soluble form, for example in the form of a water-soluble salt, or aqueous injection suspensions that comprise viscosity-increasing substances, for example sodium carboxymethylcellulose, sorbitol and/or dextran and, if desired, stabilisers. The active ingredient, optionally together with excipients, can also be in the form of a lyophilisate and can be made into a solution prior to parenteral administration by the addition of suitable solvents.

Solutions used, for example, for parenteral administration can also be used as infusion solutions.

Preferred preservatives are, for example, antioxidants, such as ascorbic acid, or microbicides, such sorbic acid or benzoic acid.

The invention relates also to a process or a method for treating one of the pathological conditions mentioned above, especially a disease responsive to inhibition of VEGF receptor tyrosine kinase or inhibition of angiogenesis, especially a corresponding tumour disease, or also psoriasis. The compounds of formula I (or an N-oxide thereof) can be administered prophylactically or therapeutically as such or in the form of pharmaceutical compositions, preferably in an amount that is effective against the mentioned diseases, to a warm-blooded animal, for example a human being, requiring such treatment, the compounds being used especially in the form of pharmaceutical compositions. In the case of a body weight of approximately 70 kg, a daily dose of from approximately 0.1 g to approximately 5 g, preferably from approximately 0.5 g to approximately 2 g, of a compound of the present invention is administered.

The present invention relates also, especially, to the use of a compound of formula I (or an N-oxide thereof), or of a pharmaceutically acceptable salt thereof, especially of a compound of formula I mentioned as being preferred, or a pharmaceutically acceptable salt thereof, as such or in the form of a pharmaceutical formulation with at least one pharmaceutically acceptable carrier, for the therapeutic and also prophylactic treatment of one or more of the above-mentioned diseases, especially of a tumour disease, or also of psoriasis, especially when that disease is responsive to inhibition of angiogenesis or to inhibition of VEGF receptor tyrosine kinase.

The present invention relates also, especially, to the use of a compound of formula I (or an N-oxide thereof), or of a pharmaceutically acceptable salt thereof, especially of a compound of formula I mentioned as being preferred, or a pharmaceutically acceptable salt thereof, as such or in the form of a pharmaceutical formulation with at least one pharmaceutically acceptable carrier, for the therapeutic and also prophylactic treatment of one or more of the above-mentioned diseases, preferably of a disease responsive to inhibition of VEGF receptor tyrosine kinase or to inhibition of angiogenesis, especially of a tumour disease or also of psoriasis, more especially when that disease is responsive to inhibition of VEGF receptor tyrosine kinase or of angiogenesis.

The present invention relates also, especially, to the use of a compound of formula I (or an N-oxide thereof), or of a pharmaceutically acceptable salt thereof, especially of a compound of formula I mentioned as being preferred, or a pharmaceutically acceptable salt thereof, for the preparation of a pharmaceutical formulation for the therapeutic and also prophylactic treatment of one or more of the above-mentioned diseases, especially of a tumour disease or also of psoriasis, especially when that disease is responsive to inhibition of VEGF receptor tyrosine kinase or of angiogenesis.

The preferred dosage, composition and preparation of pharmaceutical formulations (medicaments) to be used in each particular case are described above.

Starting Materials

The present invention relates also to novel starting materials and/or intermediates, and to processes for their preparation. The starting materials used and the reaction conditions chosen are preferably such that the compounds mentioned as being preferred are obtained.

The starting materials of formulae II and III are known, can be prepared by processes known per se, or are available commercially; in particular, they can be prepared by processes analogous to those mentioned in the Examples.

In the preparation of starting materials, any functional groups present that are not to take part in the reaction may be in protected form, if necessary. Preferred protecting groups, their introduction and their removal are described under process a) or in the Examples. Instead of the starting materials and intermediates in question, it is also possible to react salts thereof where salt-forming groups are present and the reaction in question is also possible using a salt. Therefore, any reference hereinbefore and hereinafter to starting materials is also intended to include their salts, where expedient and possible.

Compounds of formula II wherein G is —CH$_2$—O—, —CH$_2$—S—, —CH$_2$—NH—, oxa, thia or imino and the other symbols are as defined for formula I can be prepared, for example, by reacting a compound of formula IV

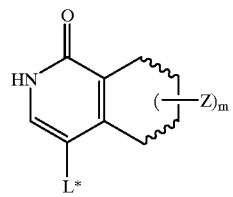

(IV)

wherein L* is a nucleofugal leaving group, especially halo, such as bromo, and m and Z and the bonds indicated by wavy lines are as defined for a compound of formula I (especially m=0, i.e. Z is not present—the corresponding compound of formula IV wherein L* is bromo is available commercially from SPECS & BIOSPECS, Rijskwijk, Holland), with a compound of formula V

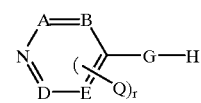

(V)

wherein G is —CH$_2$—O—, —CH$_2$—S— or —CH$_2$—NH—, or is oxa, thia or imino, and A, B, D, E, Q and r are as defined for compounds of formula I, preferably under conditions analogous to those mentioned under process a) for the reaction of a compound of formula II with a compound of formula III, or with palladium complex catalysis with Pd$^0$, for example with tetrakis(triphenylphosphinyl) palladium complexes, palladium(0)-P(o-tolyl)$_3$ complexes, palladium(0) complexes with chelating bis(phosphines) (see, for example, J. Org. Chem. 61, 7240–7241 (1996)) or the like, preferably with Pd$^0$ in the presence of an alkali metal carbonate, such as K$_2$CO$_3$, in a suitable solvent, such as toluene, at elevated temperature, preferably under reflux. There is then obtained a compound of formula II*

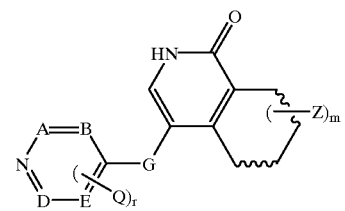

(II*)

wherein m and Z and the bonds indicated by wavy lines, and A, B, D, E, Q and r are as defined for a compound of formula I, and wherein G is —CH$_2$—O—, —CH$_2$—S— or —CH$_2$—NH—, or is oxa, thia or imino.

The corresponding compound of formula II can be prepared therefrom by introduction of a nucleofugal group L, as defined for formula II, using a corresponding acid anhydride, for example phosphoryl chloride (POCl$_3$) for the introduction of L=Cl or a different reagent mentioned below for the conversion of a compound of formula XII into a compound of formula II.

The starting materials of formulae IV and V are known, can be prepared by processes known per se, or are available commercially; in particular, they can be prepared by processes analogous to those mentioned in the Examples.

A compound of formula II wherein G is methylene and the other symbols are as defined for a compound of formula I can be prepared, for example, by reacting a lactone of formula VI

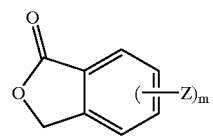

(VI)

wherein Z and m are as defined for a compound of formula I, with an alkali metal cyanide, especially potassium cyanide, at elevated temperature, for example at from 100° C. to 200° C. (see Org. Synthesis, Coll. Vol. 3, 174), yielding a cyanomethylbenzoic acid of formula VII (VII)

wherein the radicals are as defined for formula VI; the compound of formula VII is then converted into the lower alkyl ester, for example by adding a suitable di-lower alkylformamide di-lower alkylacetyl, such as dimethylformamide dimethylacetyl, to the compound of formula VII in a suitable solvent, for example a halo-lower alkane, such as dichloromethane, and stirring the mixture to complete the reaction, preferably at temperatures of from 0 to 60° C., for example at approximately room temperature. The corresponding lower alkyl ester of formula VIII is obtained (VIII)

wherein Alk is lower alkyl, especially methyl, and the other radicals are as defined for formula VI. The ester is then reacted in a suitable solvent, for example an ether, such as tetrahydrofuran, or an ester, such as ethyl propionate, or mixtures thereof, with an aldehyde of formula IX (IX)

wherein A, B, D, E, Q and r are as defined for a compound of formula I, in the presence of an alcohol, such as methanol, and of the corresponding alcoholate, such as an alkali metal methanolate, for example sodium methanolate, at a temperature of preferably from 0° C. to reflux temperature, preferably at approximately from 5 to 30° C., yielding the compound of formula X (X)

wherein the radicals A, B, D, E, Q and Z and the indices r and m are as defined for a compound of formula I; that compound is converted (under conditions analogous to those for the preparation of the lower alkyl ester of formula VII) into the corresponding lower alkyl ester of formula XI (XI)

wherein Alk is lower alkyl, especially methyl, and the other radicals are as defined for formula X. Subsequent hydrogenation in the presence of a suitable catalyst, especially a framework catalyst, such as Raney cobalt or, especially, Raney nickel, in a suitable solvent, such as an ether, for example tetrahydrofuran, or an alcohol, such as methanol, or mixtures thereof, at preferred temperatures of from 10 to 80° C., at pressures of from 0.5 to 100 bar, especially approximately at normal pressure, yields an isoquinoline compound of formula XII (XII)

wherein the radicals A, B, D, E, Q and Z and the indices r and m are as defined for a compound of formula I.

The compound of formula XII is then converted into the corresponding compound of formula II, or a salt thereof, by means of a suitable reagent for the introduction of the nucleofugal leaving group, for example a phosphoryl halide or phosphorus pentahalide, especially phosphoryl chloride ($POCl_3$) or phosphorus pentachloride, without a solvent or in a suitable solvent, for example acetonitrile, in the absence or, preferably, in the presence of a corresponding acid, for example of a hydrohalic acid, such as hydrochloric acid, at preferred temperatures of from 40° C. to reflux temperature, preferably at approximately from 40 to 60° C.

In an analogous manner, it is possible using compounds analogous to those of formula IX wherein, however, the place of the —CHO— group is taken by a corresponding lower alkane-aldehyde group, via compounds analogous to those of formulae X to XII wherein the place of the methylidene group (formula X, XI) or of the methylene group (formula XII) is taken by a corresponding lower alkylidene or lower alkylene group, to prepare corresponding compounds of formula II wherein G is lower alkylene.

The other starting materials are known, can be prepared by processes known per se, or are available commercially, or, in particular, can be prepared by processes analogous to those mentioned in the Examples.

EXAMPLES

The Examples which follow serve to illustrate the invention without limiting the scope thereof.

Temperatures are measured in degrees Celsius. Unless indicated otherwise, reactions are carried out at room temperature.

HPLC gradients:

grad$_{20-100}$ 20%→100% a) in b) for 13 min.+5 min. 100% a), grad$_{5-40}$ 5%→40% a) in b) for 7.5 min.+7 min. 40% a).

Eluant a): acetonitrile+0.05% TFA; eluant b): water+0.05% TFA. Column (250×4.6 mm) filled with C18-Nucleosil reversed phase material (5 μm average particle size, silica gel covalently derivatised by octadecylsilanes, Macherey & Nagel, Düren, FRG). Detection by UV absorption at 254 nm. The retention times ($t_{ret}$) are given in minutes. Flow rate 1 m/min.

The other short names and abbreviations used have the following meanings:

| | |
|---|---|
| abs. | absolute (solvent anhydrous) |
| Anal. calc, | calculated (theoretical) proportions of the elements in elemental analysis |
| Anal. found | proportions of the elements actually measured in elemental analysis |
| DMSO | dimethyl sulf oxide |
| ether | diethyl ether |
| FAB-MS | fast atom bombardment mass spectroscopy |
| found | see Anal. found |
| m.p. | melting point |
| brine | saturated sodium chloride solution |
| THF | tetrahydrofuran (distilled over sodium/benzophenone) |

The following starting materials are obtained from the sources indicated in each case:

3,5-Dimethylaniline, 4-chloroaniline, 3-methylaniline, 3-chloroaniline, aniline, benzylamine, 4-methoxyaniline, 3-methoxyaniline, 4-aminoacetanilide, (S)-1-phenylethylamine, (R)-1-phenylethylamine, 4-aminobenzotrifluoride (=4-(trifluoromethyl)-aniline), 4-fluoroaniline, 1,3-phenylenediamine, methanesulfonic acid, 3,4-dichloroaniline, 4-bromoaniline: Fluka, Buchs, Switzerland.

3-Benzyloxyaniline, 2-aminophenol, 4-aminophenol: Aldrich, Buchs, Switzerland.

3-Bromo-5-trifluoromethyl-aniline (Fluorochem, Old Glossop, Great Britain); 4-chloro-3-trifluoromethyl-aniline (Fluka, Buchs, Switzerland).

Example 1

1-(3,5-Dimethylanilino)-4-[(pyridin-4-yl)-methyl]-isoquinoline (=N-(3,5-dimethyl-phenyl)-[4-(pyridin-4-yl-methyl)-isoquinolin-1-yl]-amine)

With the exclusion of moisture, 100 mg (0.825 mmol) of 3,5-dimethyl-aniline are dissolved in 4 ml of ethanol, and 196 μl (0.784 mmol) of HCl (4N in dioxane) are added. After the addition of 200 mg (0.785 mmol) of 1-chloro-4-[(pyridin-4-yl)-methyl]-isoquinoline, the mixture is heated for 8 hours at 90° C. Concentration by evaporation is then carried out; the residue is taken up in 4 ml of water, 1 ml of saturated ammonia solution and 20 ml of CH$_2$Cl$_2$, and the organic phase is separated off, dried with Na$_2$SO$_4$ (anhydrous) and concentrated by evaporation again. Column chromatography (SiO$_2$; ethyl acetatelhexane 3:1) and crystallisation from ethyl acetate/hexane yield the title compound: m.p. 156–158° C.; $^1$H NMR (DMSO-d$_6$) 9.00 (s, HN), 8.54 (d, 1H), 8.42 (d, 2H), 8.00 (s, 1H), 7.80 (d, 1H), 7.65 (m, 2H), 7.50 (s, 2H), 7.26 (d, 2H), 6.64 (s, 1H), 4.25 (s, 2H), 2.27 (s, 6H); FAB-MS: (M+H)$^+$=340; Anal. calc. (C$_{23}$H$_{21}$N$_3$.0.1H$_2$O) C 80.95%, H 6.26%, N 12.31%; found C 80.9%, H 6.2%, N 12.4%.

The starting material is prepared as follows:

1a) 2-Cyanomethyl-benzoic Acid Methyl Ester

With gentle heating, 175 g (1.08 mol) of 2-cyanomethyl-benzoic acid (for preparation see: *Org. Synthesis,* Coll, Vol. 3,174) are dissolved in 1.7 liters of CH$_2$Cl$_2$; 242 ml (=90%, 1.6 mol) of dimethylformamide dimethylacetal are added dropwise at room temperature, and stirring is carried out for 38 hours to complete the reaction. The reaction mixture is washed with 2×1.2 liters of saturated NaHCO$_3$ solution and brine. The aqueous phases are extracted using 2 portions of CH$_2$Cl$_2$, and the organic phases are dried (Na$_2$SO$_4$) and concentrated by evaporation. Column chromatography (SiO$_2$; ethyl acetate/hexane 1:4, applied in ethyl acetate/hexane/CH$_2$Cl$_2$) yields the title compound: m.p. 49–50° C.; $^1$H NMR (DMSO-d$_6$) 7.96 (d, 1H), 7.66 (t, 1H), 7.57 (d, 1H), 7.51 (t, 1H), 4.26 (s, 2H), 3.86 (s, 3H); Anal. calc. (C$_{10}$H$_9$NO$_2$) C 68.56%, H 5.18%, N 8.00%; found C 68.5%, H 5.1%, N 7.9%.

1b) 2-[(1-Cyano-2-(pyridin-4-yl)-vinyl]-benzoic Acid

With the exclusion of air, 127.7 ml (1.35 mol) of pyridine-4-carbaldehyde (Fluka, Buchs, Switzerland) are added to a solution of 215.6 g (1.23 mol) of 2-cyanomethyl-benzoic acid methyl ester in 1.8 liters of THF. The mixture is cooled to 8–9° C., 297 ml (1.6 mol) of a 5.4M solution of sodium methanolate in methanol are added dropwise in the course of 20 minutes, and the mixture is stirred for 1.5 hours at from 10 to 15° C. The mixture is then adjusted to pH 6.0 using approximately 350 ml of 4N HCl and is then stirred for one hour at 5° C. The title compound crystallises out and is filtered off with suction and washed thoroughly with THF/water 2:1 and THF: m.p. 218–219° C.; FAB-MS: (M+H)$^+$= 251; $^1$H NMR (DMSO-d$_6$) 13.4 (sb, 1H), 8.76 (d, 2H), 7.98 (d, 1H), 7.77 (d, 2H), 7.72 (t, 1H), 7.62 (m, 2H), 7.52 (s, 1H); Anal. calc. (C$_{15}$H$_{10}$N$_2$O$_2$) C 71.99%, H 4.03%, N 11.19%; found C 71.9%, H 4.1%, N 11.1%.

1c) 2-[(1-Cyano-2-(pyridin-4-yl)-vinyl]-benzoic Acid Methyl Ester

With the exclusion of moisture, 211 g (0.843 mol) of 2-[(1-cyano-2-(pyridin-4-yl)-vinyl]-benzoic acid are suspended in 3.3 liters of CH$_2$Cl$_2$; 169 ml (=90%, 1.1 mol) of dimethylformamide dimethylacetal (Fluka, Buchs, Switzerland) are added at room temperature, and stirring is carried out for 22 hours to complete the reaction. The reaction mixture is filtered, and the residue is washed thoroughly with CH$_2$Cl$_2$ and discarded. Concentration of the filtrate by evaporation, chromatography (SiO$_2$; ethyl acetate) and crystallisation from ethyl acetate/hexane yield the title compound: m.p. 102–104° C.; FAB-MS: (M+H)$^+$=265; $^1$H NMR (DMSO-d$_6$) 8.76 (d, 2H), 7.97 (d, 1H), 7.76 (m, 3H), 7.65 (m, 2H), 7.60 (s, 1H), 3.86 (s, 3H); Anal. calc.

($C_{16}H_{12}N_2O_2$) C 72.72%, H 4.58%, N 10.60%; found C 72.7%, H 4.8%, N 10.5%.

1d) 4-(Pyridin-4-yl-methyl)-2H-isoquinolin-1-one

In the presence of 5×40 g of Raney nickel (added at intervals), 163 g (617 mmol) of 2-[(1-cyano-2-(pyridin-4-yl)-vinyl]-benzoic acid methyl ester are hydrogenated in 3 liters of THF at 40° C. for 90 hours. The reaction mixture is filtered, and the filtrate is concentrated by evaporation and crystallised from acetonitrile/ethyl acetate (→title compound). Further product can be obtained from the mother liquor by chromatography ($SiO_2$; ethyl acetate→acetone): m.p. 189–190° C.; FAB-MS: $(M+H)^+$= 237; $^1H$ NMR (DMSO-$d_6$) 11.27 (sb, HN), 8.45 (d, 2H), 8.23 (d, 1H), 7.65 (t, 1H), 7.48 (m, 2H), 7.27 (d, 2H), 7.18 (s, 1H), 4.05 (s, 2H); Anal. calc. ($Cl_5H_{12}N_2O.0.05\ H_2O$) C 75.96%, H 5.14%, N 11.81%; found C 75.8%, H 5.2%, N 11.9%.

1e) 1-Chloro-4-(pyridin-4-methyl)-isoquinoline

With the exclusion of air, 32.7 g (139 mmol) of 4-(pyridin-4-yl-methyl)-2H-isoquinolin-1-one are made into a slurry in 560 ml of acetonitrile, and 69.2 ml (277 mmol) of 4N HCl in dioxane and 31.7 ml (346 mmol) of $POCl_3$ are added. The mixture is stirred for 22 hours at 50° C. and then cooled in an ice bath, and a solution of 128.6 g of $NaHCO_3$ in 1.64 liters of water is added in the course of 30 minutes. During the addition, first a clear solution forms and then the title compound precipitates and, after 15 minutes, can be filtered off, washed thoroughly with water and ether and dried under a high vacuum at 60° C.: m.p. 119–120° C.; FAB-MS: $(M+H)^+$=255; $^1H$ NMR (DMSO-$d_6$) 8.43 (d, 2H), 8.33 (s, 1H), 8.31 (d, 1H), 8.07 (d, 1H), 7.85 (m, 2H), 7.25 (d, 2H), 4.45 (s, 2H).

The following are prepared analogously to Example 1 or to the processes mentioned in this disclosure:

Product of formula I

| Example | Starting material $H_2N-Y$ | Product | m.p. [° C.] | Anal.* | FAB MS $(M + H)^+$ |
|---|---|---|---|---|---|
| 2 | 4-chloroaniline | N-methyl-4-chloroaniline derivative | 182–183 | CHN | 346 |
| 3 | 3-bromo-5-(trifluoromethyl)aniline | corresponding product | 188–189 | CHN | 458/460 |
| 4 | 4-chloro-3-(trifluoromethyl)aniline | corresponding product | 205–206 | CHN | 414 |
| 5 | 3-methylaniline | corresponding product | 118–119 | CHN | 326 |

*Elemental analysis for the element in question with = 0.4% deviation from the theoretical yield The following compounds are prepared by the processes mentioned above:
Product of formula I
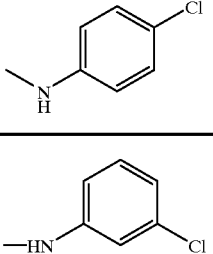
| Example | H-N-Y structure | m | Z | m.p. [° C.] | Anal.* | FAB MS (M + H)+ |
|---|---|---|---|---|---|---|
| 6 | —HN–C₆H₄–Cl (4-Cl) | 0 | — | | | |
| 7 | —HN–C₆H₄–Cl (3-Cl) | 0 | — | | | |
| 8 | —HN–phenyl | 0 | — | | | |
| 9 | —HN–C₆H₃(CH₃)(Br) | 0 | — | 167–168 | CHNBr | 404/406 |
| 10 | —HN–C₆H₄–OCH₃ | 0 | — | | | |
| 11 | —HN–C₆H₄–O–CH₂–C₆H₅ | 0 | — | | | |
| 12 | —HN–C₆H₄–OCH₃ (3-OCH₃) | 0 | — | | | |
| 13 | —HN–C₆H₄–NHC(O)CH₃ | 0 | — | | | |

-continued

Product of formula I

[Reaction scheme: Starting material (1-chloro-4-(pyridin-4-ylmethyl)isoquinoline derivative with (Z)ₘ substituent) + H₂N-Y → Product (1-(HN-Y)-4-(pyridin-4-ylmethyl)isoquinoline derivative with (Z)ₘ substituent)]

| Example | H-N-Y (amine) | m | Z | m.p. [° C.] | Anal.* | FAB MS (M + H)⁺ |
|---|---|---|---|---|---|---|
| | (reference: 4-chloro-N-methylanilino group shown) | | | | | |
| 13 | —HN—CH(CH₃)—C₆H₅ (S) | 0 | — | | | |
| 14 | —HN—CH(CH₃)—C₆H₅ (R) | 0 | — | | | |
| 15 | —HN—(2-methoxyphenyl) | 0 | — | | | |
| 16** | —HN—(pyridin-3-yl) | 0 | — | | | |
| 17 | —HN—(4-CF₃-phenyl) | 0 | — | 160–161 | CHNF | 380 |
| 18 | —HN—(4-fluorophenyl) | 0 | — | | | |
| 19 | —HN—(3-hydroxyphenyl) | 0 | — | | | |

-continued
Product of formula I
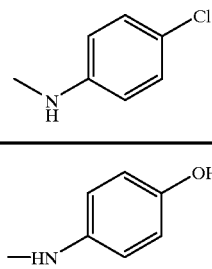
| Example | | m | Z | m.p. [° C.] | Anal.* | FAB MS (M + H)+ |
|---|---|---|---|---|---|---|
| 20 | 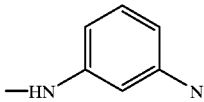 | 0 | — | | | |
| 21 | 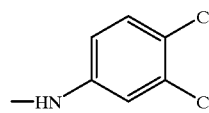 | 0 | — | | | |
| 22 | 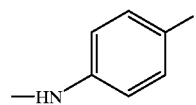 | 0 | — | | | |
| 23 | 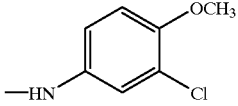 | 0 | — | | | |
| 24 | 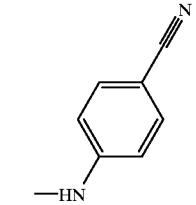 | 0 | — | | | |
| 25 | 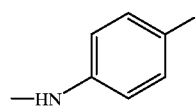 | 0 | — | | | |
| 26 | 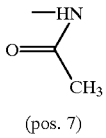 | 1 | —HN—C(O)—CH₃ (pos. 7) | | | |

-continued

Product of formula I

Starting material → Product (reaction scheme with chloroisoquinoline + H-NHY → aminoisoquinoline)

| Example | HN(CH₃)-C₆H₄-Cl (4-chloro-N-methylanilino group, fixed) | —HN-Ar substituent | m | Z | m.p. [° C.] | Anal.* | FAB MS (M + H)⁺ |
|---|---|---|---|---|---|---|---|
| 27 | | —HN—C₆H₄—OCH₃ (para) | 1 | —HN—C(=O)—CH₃ (pos. 7) | | | |
| 28 | | —HN—C₆H₄—OCH₃ (meta) | 1 | —HN—C(=O)—CH₃ (pos. 7) | | | |
| 29 | | —HN—C₆H₄—Cl (meta) | 1 | —HN—C(=O)—CH₃ (pos. 7) | | | |
| 30 | | —HN—C₆H₅ | 1 | —HN—C(=O)—CH₃ (pos. 7) | | | |
| 31 | | —HN—C₆H₄—Br (para) | 1 | —HN—C(=O)—CH₃ (pos. 7) | | | |
| 32 | | —HN—C₆H₄—Cl (meta) | 1 | —HN—C(=O)—O—CH₂—C₆H₅ (pos. 7) | | | |

-continued

Product of formula I

| Example | H-N(Y)H structure | m | Z | m.p. [°C.] | Anal.* | FAB MS (M + H)+ |
|---|---|---|---|---|---|---|
| 33 | —HN—(3-Cl-C6H4) | 1 | —NH₂ (pos. 7) | | | |
| 34 | —HN—(3-Cl-C6H4) | 1 | —HN—C(O)—(3-NO₂-C6H4) (pos. 7) | | | |
| 35 | —HN—(3-Cl-C6H4) | 1 | —HN—C(O)—(3-NH₂-C6H4) (pos. 7) | | | |
| 36 | —HN—(3-Cl-C6H4) | 1 | —NH(CH₃)—CH₂—CH₂—OH (pos. 7) | | | |
| 37 | —HN—(4-Cl-C6H4) | 1 | —Br (pos. 7) | | | |

-continued
Product of formula I
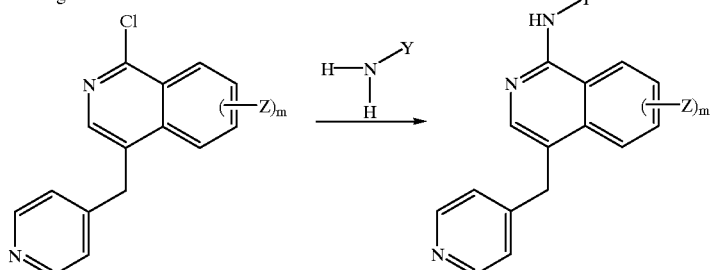
| Example | [structure] | m | Z | m.p. [° C.] | Anal.* | FAB MS (M + H)+ |
|---|---|---|---|---|---|---|
| 38 | —HN—C6H4—CH3 (4-CH3) | 0 | — | | | |
| 39 | —HN—C6H3(F)(Cl) (4-F, 3-Cl) | 0 | — | | | |
| 40 | —HN—C6H4—CH3 (3-CH3) | 0 | — | | | |
| 41 | —HN—C6H4—C2H5 (4-C2H5) | 0 | — | | | |
| 42 | —HN—C6H4—C3H7 (4-propyl) | 0 | — | 118–119 | CHN | 354 |
| 43 | —HN—C6H3(CH3)(F) (4-CH3, 3-F) | 0 | — | | | |
| 44 | —HN—C6H3(Cl)(F) (4-Cl, 2-F) | 0 | — | | | |
| 45 | —HN—C6H3(CH3)(CH3) (4-CH3, 3-CH3) | 0 | — | 144–145 | CHN | 340 |

-continued

Product of formula I

Starting material → Product (1-chloro-4-(pyridin-4-ylmethyl)isoquinoline + H-NH-Y → 1-(Y-amino)-4-(pyridin-4-ylmethyl)isoquinoline)

| Example | H-N(H)-R (amine) | m | Z | m.p. [°C] | Anal.* | FAB MS (M + H)+ |
|---|---|---|---|---|---|---|
| | 4-Cl-C6H4-N(H)(CH3) | | | | | |
| 46 | 4-isopropyl-C6H4-NH— | 0 | — | 158–159 | CHN | 354 |
| 47 | 4-tert-butyl-C6H4-NH— | 0 | — | 158–159 | CHN | 368 |
| 48 | 4-OCH2CH3-C6H4-NH— | 0 | — | | | |
| 49 | 4-phenyl-C6H4-NH— | 0 | — | | | |
| 50 | 2,3,4-tri(OCH3)-C6H2-NH— | 0 | — | | | |
| 51 | cyclohexyl-NH— | 0 | — | | | |

-continued

Product of formula I

Starting material → with H-N(H)-Y gives product where Cl is replaced by HN-Y on the isoquinoline.

| Example | HN-Y group | m | Z | m.p. [° C.] | Anal.* | FAB MS (M + H)+ |
|---|---|---|---|---|---|---|
| | N-methyl-(4-chlorophenyl)amine | | | | | |
| 52 | —HN-cyclopentyl | 0 | — | | | |
| 53 | —HN-cyclopropyl | 0 | — | | | |
| 54 | —HN-(4-phenoxyphenyl) | 0 | — | | | |
| 55 | —HN-(5-methyl-2-hydroxyphenyl) (CH₃ and OH substituents) | 0 | — | | | |
| 56 | —NH-(4-methoxy-3-hydroxyphenyl) | 0 | — | | | |
| 57 | —NH-(3-methylthiophenyl) | 0 | — | | | |
| 58 | —NH-(3-ethylphenyl) | 0 | — | 146–148 | CHN | 340 |

-continued

Product of formula I

Starting material → Product (1-chloro-4-(pyridin-4-ylmethyl)isoquinoline + H-NH-Y → 1-(Y-amino)-4-(pyridin-4-ylmethyl)isoquinoline derivatives)

| Example | HN(CH₃)–Ar (amine) | m | Z | m.p. [°C] | Anal.* | FAB MS (M + H)⁺ |
|---|---|---|---|---|---|---|
| | 4-chloro-N-methylaniline (header structure) | | | | | |
| 59 | 3-ethoxy-N-methylaniline | 0 | — | | | |
| 60 | 3-(trifluoromethyl)-N-methylaniline | 0 | — | 159–160 | CHN | 380 |
| 61 | 3-(trifluoromethoxy)-N-methylaniline | 0 | — | | | |
| 62 | 3-bromo-N-methylaniline | 0 | — | 169–170 | CHNBr | 390/392 |
| 63 | 3-(hydroxymethyl)-N-methylaniline | 0 | — | | | |
| 64 | 3-(1-hydroxyethyl)-N-methylaniline | 0 | — | | | |
| 65 | 3-isopropoxy-N-methylaniline | 0 | — | | | |

-continued

Product of formula I

Starting material reaction scheme: 1-chloro-4-(pyridin-4-ylmethyl)isoquinoline with $(Z)_m$ substituents reacts with $H-NH-Y$ to give 1-(NHY)-4-(pyridin-4-ylmethyl)isoquinoline with $(Z)_m$ substituents.

| Example | H-N(H)-Y (4-chloroaniline shown as reference structure) | m | Z | m.p. [°C.] | Anal.* | FAB MS (M + H)+ |
|---|---|---|---|---|---|---|
| 66 | 3-methoxy-5-(trifluoromethyl)aniline (NH-phenyl with OMe and CF₃) | 0 | — | | | |
| 67 | 3,5-dimethoxyaniline (NH-phenyl with two OMe) | 0 | — | | | |
| 68 | 3-tert-butylaniline | 0 | — | 147–148 | CHN | 368 |
| 69 | 3-isopropylaniline | 0 | — | 143–145 | CHN | 354 |
| 70 | 3-fluoro-5-(trifluoromethyl)aniline | 0 | — | 205–205 | CHNF | 398 |
| 71 | 3-(2,2,3,3-tetrafluoropropyl)aniline | 0 | — | | | |

-continued
Product of formula I
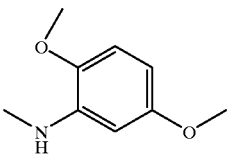
| Example | HN-Y structure | m | Z | m.p. [° C.] | Anal.* | FAB MS (M + H)+ |
|---|---|---|---|---|---|---|
| 72 | 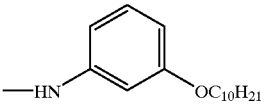 | 0 | — | | | |
| 73 | 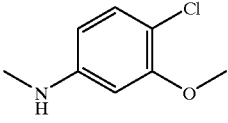 | 0 | — | | | |
| 74 | 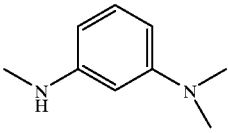 | 0 | — | | | |
| 75 | 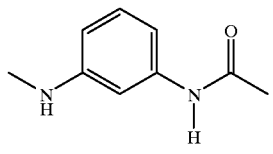 | 0 | — | | | |
| 76 | 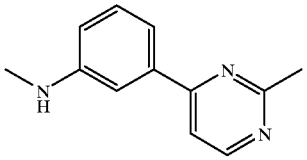 | 0 | — | | | |
| 77 | | 0 | — | | | |

-continued
Product of formula I
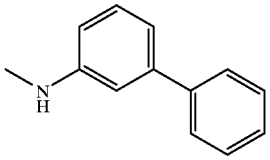
| Example | | m | Z | m.p. [° C.] | Anal.* | FAB MS (M + H)+ |
|---|---|---|---|---|---|---|
| 78 | 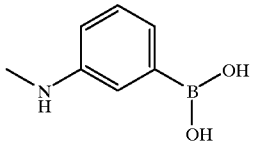 | 0 | — | | | |
| 79 | 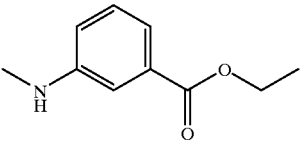 | 0 | — | | | |
| 80 | 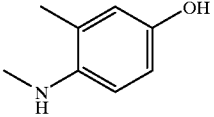 | 0 | — | | | |
| 81 | 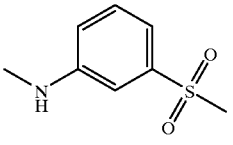 | 0 | — | | | |
| 82 | 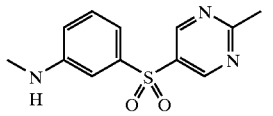 | 0 | — | | | |
| 83 | 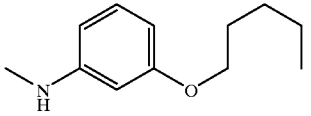 | 0 | — | | | |
| 84 | | 0 | — | | | |

-continued
Product of formula I
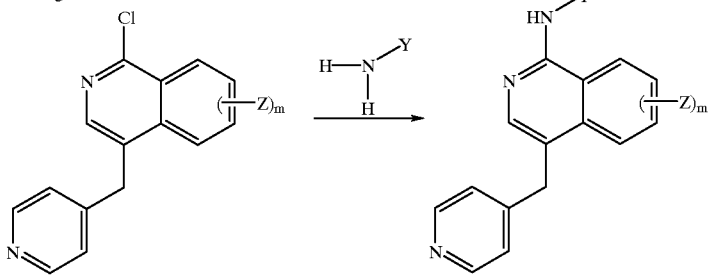
| Example | [structure] | m | Z | m.p. [° C.] | Anal.* | FAB MS (M + H)+ |
|---|---|---|---|---|---|---|
| 85 | [3-(oxazol-5-yl)phenyl]methylamino | 0 | — | | | |
| 86 | [4-fluoro-3-methoxyphenyl]methylamino | 0 | — | | | |
| 87 | [4-isopropyl-3-methylphenyl]methylamino | 0 | — | | CHN | 368 |
| 88 | [4-acetyl-3-hydroxyphenyl]methylamino | 0 | — | | | |
| 89 | [3-carbamoylphenyl]methylamino | 0 | — | | | |
| 90 | [benzo[1,3]dioxol-5-yl]methylamino | 0 | — | | | |

-continued

Product of formula I

[Reaction scheme: Starting material with Cl on isoquinoline bearing pyridylmethyl group + H-NHY → Product with HN-Y in place of Cl, and (Z)_m substituent]

| Example | [amine substituent structure] | m | Z | m.p. [° C.] | Anal.* | FAB MS (M + H)+ |
|---|---|---|---|---|---|---|
| | —HN—(4-chlorophenyl) (header structure) | | | | | |
| 91 | —HN—(3-acetylphenyl), C(O)CH₃ | 0 | — | | | |
| 92 | —HN—(3-(2-methyl-1,3-dioxolan-2-yl)phenyl) | 0 | — | | | |
| 93 | —HN—(4-hydroxy-3-chlorophenyl) | 0 | — | | | |
| 94 | —NH—(3-bromo-5-trifluoromethylphenyl) | 1 | NH₂ (pos. 7) | | | |
| 95 | —NH—(4-methylphenyl) | 1 | NH₂ (pos. 7) | | | |
| 96 | —NH—(4-methylphenyl) | 1 | NH₂ (pos. 7) | | | |
| 97 | —NH—(4-methoxyphenyl) | 1 | NH₂ (pos. 7) | | | |

-continued
Product of formula I
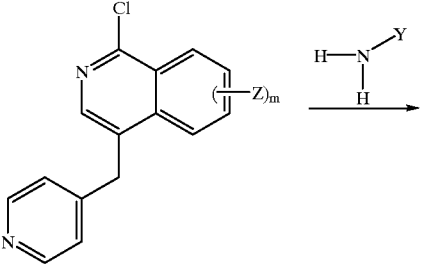
| Example | Starting material (HN-Y structure, common core: —NH—Ar) | m | Z | m.p. [°C.] | Anal.* | FAB MS (M + H)+ |
|---|---|---|---|---|---|---|
| | 4-chlorophenyl-NH— | | | | | |
| 98 | 3-methoxyphenyl-NH— | 1 | NH₂ (pos. 7) | | | |
| 99 | 3-(ureido)phenyl-NH— | 0 | — | | | |
| 100 | 4-methyl-3-methoxyphenyl-NH— | 0 | — | | CHN | 356 |
| 101 | 3-(SCF₃)phenyl-NH— | 0 | — | | | |
| 102 | 4-chloro-3-(SO₂CF₃)phenyl-NH— | 0 | — | | | |
| 103 | 4-(CONHCH₃)phenyl-NH— | 0 | — | | | |
| 104 | 3-(pyrazol-3-yl)phenyl-NH— | 0 | — | | | |

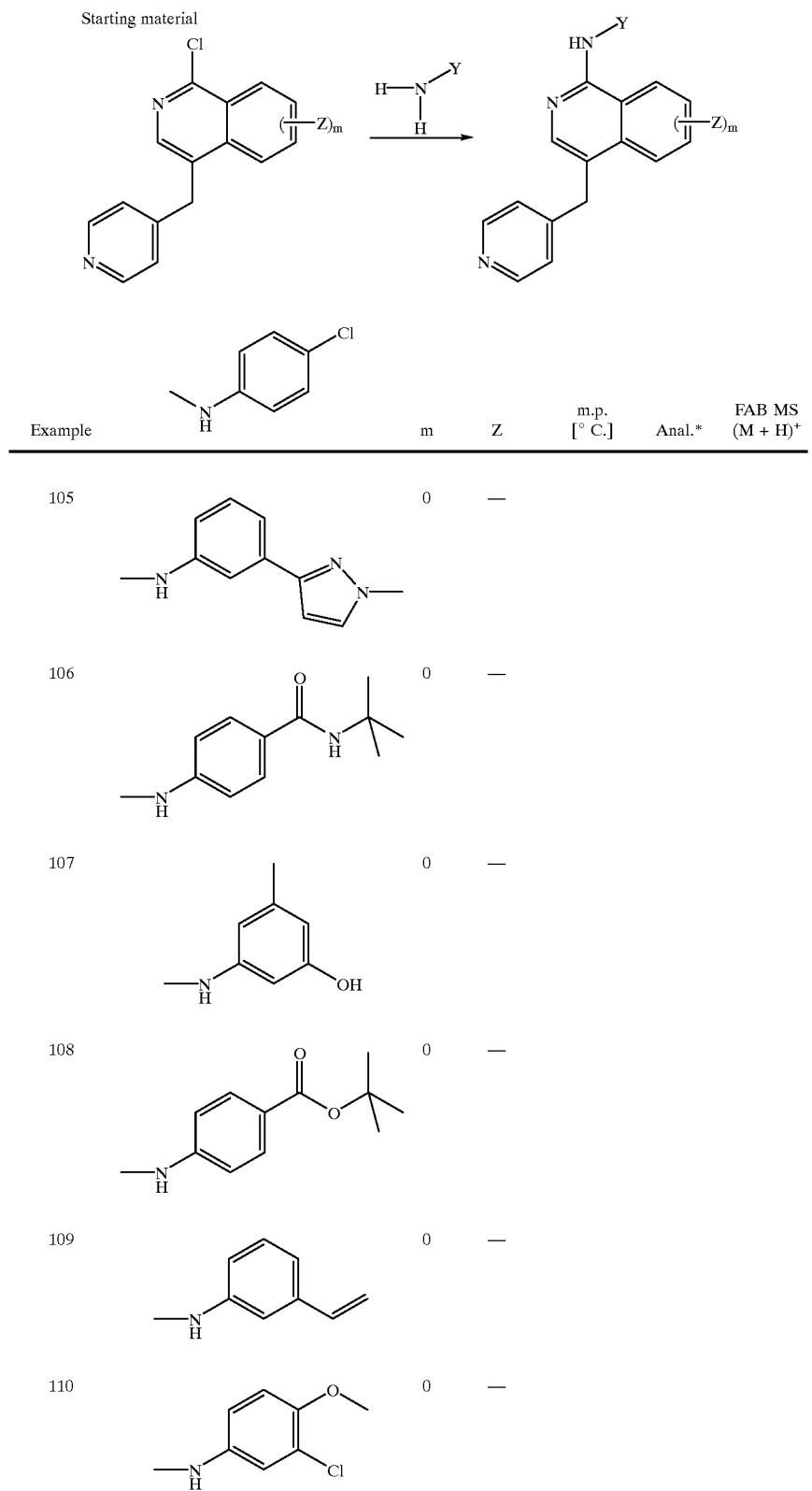

-continued
Product of formula I
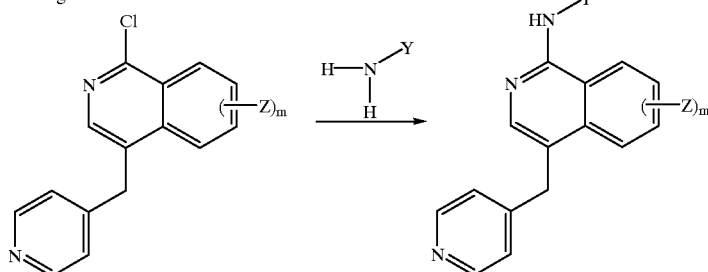
| Example | Starting material (HN group) | m | Z | m.p. [° C.] | Anal.* | FAB MS (M + H)+ |
|---|---|---|---|---|---|---|
| 111 | 4-Cl-C6H4-N(CH3)H | 0 | — | 201–202 | CHNClF | 414 |
| 112 | 3-Cl-5-CF3-C6H3-NH(CH3) | 0 | — | 215–216 | CHNF | 448 |
| 113 | 3,5-bis(CF3)-C6H3-NH(CH3) | 0 | — | 203–204 | CHNBrF | 458/460 |
| 114 | 4-Br-3-CF3-C6H3-NH- | 0 | — | | | |
| 115*** | 4-F-3-CF3-C6H3-NH- | 0 | — | 180–181 | | 506 |
| 116 | 4-I-3-CF3-C6H3-NH- | 0 | — | 149–150 | CHNI | 452 |

-continued

Product of formula I

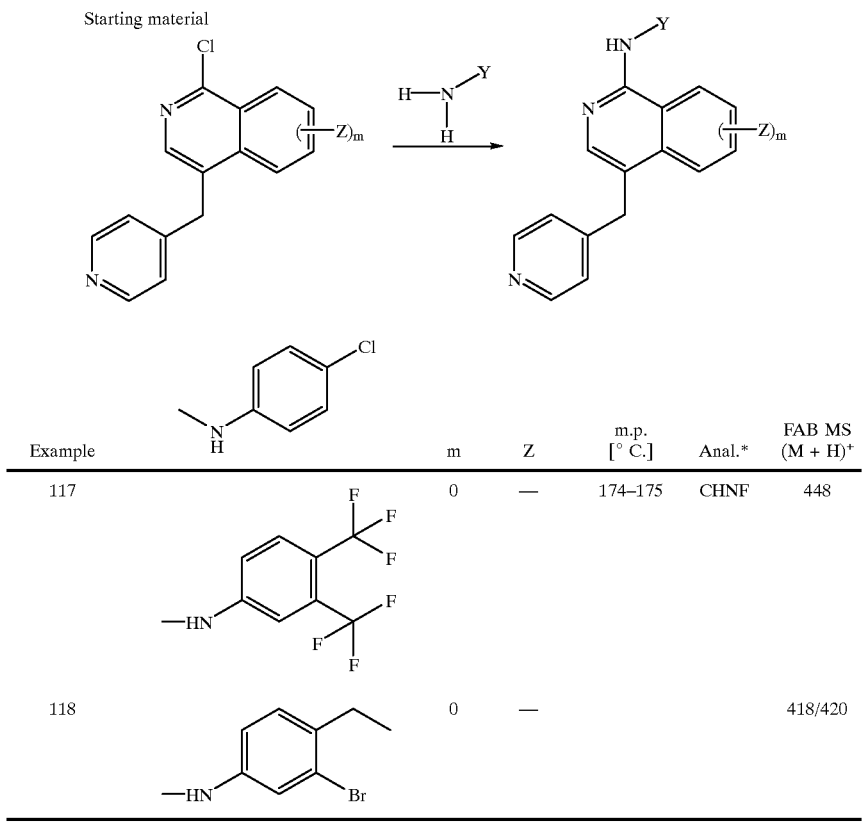

| Example | (substituent) | m | Z | m.p. [°C.] | Anal.* | FAB MS (M + H)+ |
|---|---|---|---|---|---|---|
| 117 | (4-chloro-N-methyl-anilino) | 0 | — | 174–175 | CHNF | 448 |
| | (3,4-bis(trifluoromethyl)anilino) | | | | | |
| 118 | (3-bromo-4-ethyl-anilino) | 0 | — | | | 418/420 |

*Elemental analysis for the element in question with ≦0.4% deviation from the theoretical yield

**Compound 16 can especially be prepared as follows:

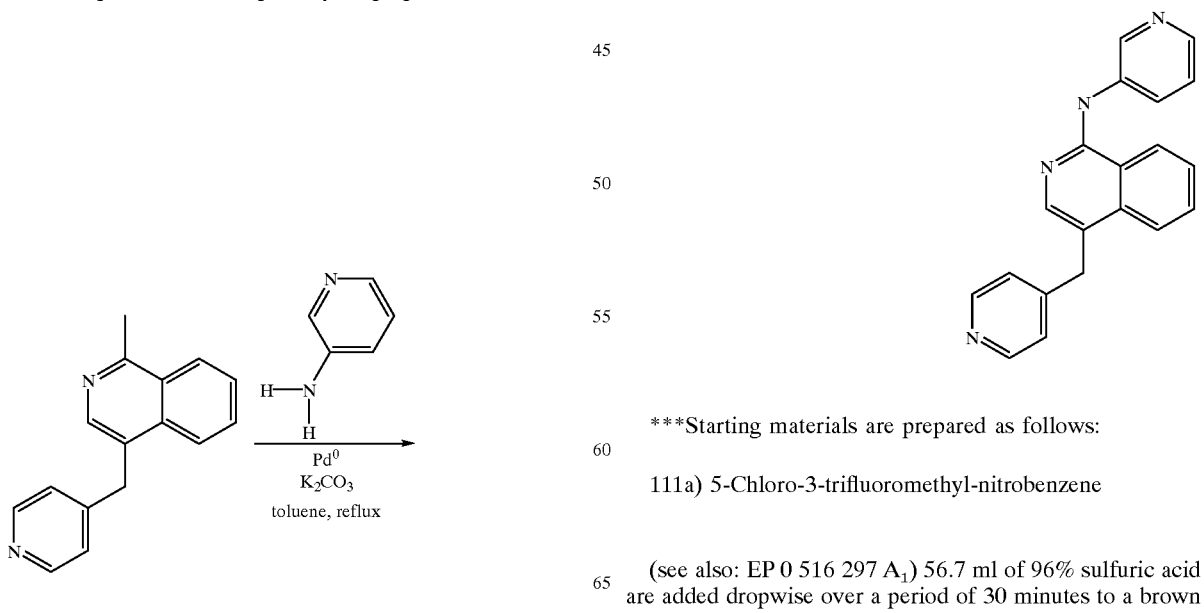

***Starting materials are prepared as follows:

111a) 5-Chloro-3-trifluoromethyl-nitrobenzene (see also: EP 0 516 297 A1) 56.7 ml of 96% sulfuric acid are added dropwise over a period of 30 minutes to a brown solution of 90 g (374 mmol) of 4-amino-3-chloro-5-nitro-benzotrifluoride (Maybridge; Tintagel/England) in 500 ml of ethanol (exothermic). After heating to 75° C., 64.53 g (935 mmol) of sodium nitrite are added in portions over a period of one hour (evolution of gas). The mixture is stirred for 2.5 hours at 75° C. and then cooled to room temperature. The reaction mixture is poured onto 1.5 liters of ice-water and extracted four times with ether. Washing the organic phases with 0.1 N HCl, saturated NaHCO$_3$solution and brine, drying (Na$_2$SO$_4$) and concentration by evaporation yield a brown oil. Column chromatography (SiO$_2$; hexane) yields the title compound in the form of an oil: $^1$H-NMR (DMSO-d$_6$) 8.62 (m, 1H), 8.46 (m, 2H), MS 225 (M)$^+$, 179 (M—NO$_2$)$^+$.

111b) 5-Amino-3-chloro-benzotrifluoride

In the presence of 10.17 g of Raney nickel, 92 g (0.408 mol) of 5-chloro-3-trifluoromethyl-nitrobenzene are hydrogenated in 1 liter of methanol. The reaction mixture is filtered over Celite/activated carbon and the residue is washed with methanol. Concentration of the filtrate by evaporation yields the oily title compound: $^1$H-NMR (DMSO-d$_6$) 6.80 (m, 3H), 5.92 (s, H$_2$N); FAB-MS (M+H)$^+$= 196.

115a) 4-Iodo-3-trifluoromethyl-nitrobenzene

Under a protecting gas, 20 g (97 mmol) of 2-amino-5-nitrobenzotrifluoride (Fluka; Buchs, Switzerland) are placed in 250 ml of H$_2$SO$_4$/H$_2$O 1:1 and cooled to 0° C., and at that temperature a solution of 6.69 g (97 mmol) of sodium nitrite in 39 ml of H$_2$O is added. After 2 hours' stirring in an ice bath, 36.94 g (194 mmol) of CuI are added in portions, whereupon a light-yellow suspension forms. After 30 minutes, the mixture is heated slowly to 80° C. (vigorous evolution of gas!) and is stirred for one hour at 80° C. Pouring into one liter of ice-water and filtering off yield mustard-yellow crystals. They are extracted using 2×150 ml of methanol and in each case filtered. Concentration of the filtrates by evaporation, column chromatography (SiO$_2$; toluene) and crystallisation from toluene yield the title compound: $^1$H NMR (DMSO-d$_6$) 8.45 (d, J=8.6 Hz, 1H), 8.36 (d, J=2.7 Hz, 1H), 8.16 (dd, J=8.6/2.7 Hz, 1H); FAB-MS: (M)$^+$=317; Anal. calc. (C$_7$H$_3$NO$_2$F$_3$I) C 26.52%, H 0.95%, N 4.42%,140.03%; C 26.53%, H 0.98%, N 4.50%, I 39.94%.

115b) 3-Amino-6-iodo-benzotrifluoride

In the presence of 1.7 g of Raney nickel, 8.6 g (27 mmol) of 4-iodo-3-trifluoromethyl-nitro-benzene are hydrogenated in 170 ml of methanol. The reaction mixture is filtered over Celite. Concentration of the filtrate by evaporation yields the oily title compound, which slowly crystallises when left to stand: $^1$H NMR (CDCl$_3$) 7.63 (d, 1H), 6.98 (d, 1H), 6.54 (dd, 1H), 5.75 (s, H$_2$N); FAB-MS (M+H)$^+$=288.

The following compounds of formula I are prepared analogously to one of the above-mentioned processes:

| Example | A | B | D | E | r | Q | G | m | Z | X | R | n | Y |
|---|---|---|---|---|---|---|---|---|---|---|---|---|---|
| 119 | C | CH | CH | CH | 1 | CH$_3$ (3'-) | CH$_2$ | 0 | — | NH | — | 0 | 4-Cl-C$_6$H$_4$-NH- |
| 120 | C | CH | CH | C | 2 | CH$_3$ (3'-, 6'-) | CH$_2$ | 0 | — | NH | — | 0 | 4-Cl-C$_6$H$_4$-NH- |
| 121 | CH | CH | CH | CH | 0 | — | CH$_2$NH | 0 | — | NH | — | 0 | 4-Cl-C$_6$H$_4$-NH- |
| 122 | CH | CH | CH | CH | 0 | — | CH$_2$O | 0 | — | NH | — | 0 | 4-Cl-C$_6$H$_4$-NH- |

-continued
| Example | A | B | D | E | r | Q | G | m | Z | X | R | n | Y |
|---|---|---|---|---|---|---|---|---|---|---|---|---|---|
| 123 | CH | CH | CH | CH | 0 | — | CH$_2$ | 0 | — | O | — | 0 | 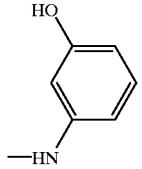 |
| 124 | CH | CH | CH | CH | 0 | — | (CH$_2$)$_2$ | 0 | — | NH | — | 0 | 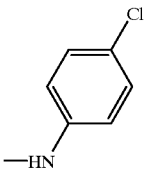 |
| 125 | CH | N | CH | CH | 0 | — | CH$_2$ | 0 | — | NH | — | 0 | 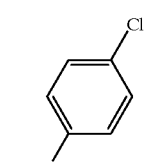 |
| 126 | CH | CH | CH | CH | 0 | — | CH$_2$ | 0 | — | O | — | 0 | 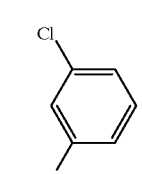 |
| 127 | CH | CH | CH | CH | 0 | — | CH$_2$ | 0 | — | O | — | 0 | 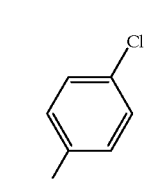 |
| 128 | CH | CH | CH | CH | 0 | — | CH$_2$ | 0 | — | O | — | 0 | 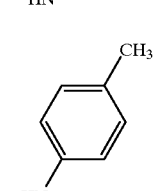 |
| 129 | CH | CH | CH | CH | 0 | — | CH$_2$ | 0 | — | O | — | 0 | 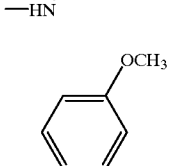 |
| 130 | CH | CH | CH | CH | 0 | — | CH$_2$ | 0 | — | S | — | 0 | 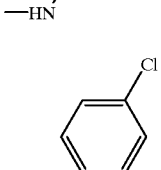 |

The Examples mentioned below are prepared analogously to the above-mentioned processes:

Example 131

1-(4-Chloro-anilino)-4-(4-pyridyl-methyl)-5,6,7,8-tetrahydro-isoquinoline

Example 132

1-(3-Chlorobenzylamino)-4-[(pyridin-4-yl)-methyl]-isoquinoline

With the exclusion of moisture, 1.6 ml (13.1 mmol) of 3-chlorobenzylamine and 800 mg (3.14 mmol) of 1-chloro-4-(pyridin-4-ylmethyl)-isoquinoline (Example 1e) are stirred for 2 hours at 150° C. The mixture is suspended in ethyl acetate, 1 ml of concentrated ammonia solution is added, washing with water and brine is carried out, and the organic phase is dried ($Na_2SO_4$) and concentrated by evaporation. Column chromatography ($SiO_2$; ethyl acetate) yields the title compound: m.p. 141–142° C.; $^1$H NMR (DMSO-$d_6$) 8.39 (d, 2H), 8.31 (d, 1H), 8.03 (t, HN), 7.82 (s, 1H), 7.69 (d, 1H), 7.61 (t, 1H), 7.50 (t, 1H), 7.40 (s, 1H), 7.33 (m, 2H), 7.26 (m, 1H), 7.20 (d, 2H), 4.73 (d, 2H), 4.14 (s, 2H); FAB-MS: (M+H)$^+$=360; Anal. calc. ($C_{22}H_{18}N_3Cl$) C 73.43%, H 5.04%, N 11.68%, Cl 9.85%; found C 73.2%, H 5.1%, N 11.6%, Cl 9.9%.

The following are prepared analogously to Example 132 or the processes mentioned in this disclosure:

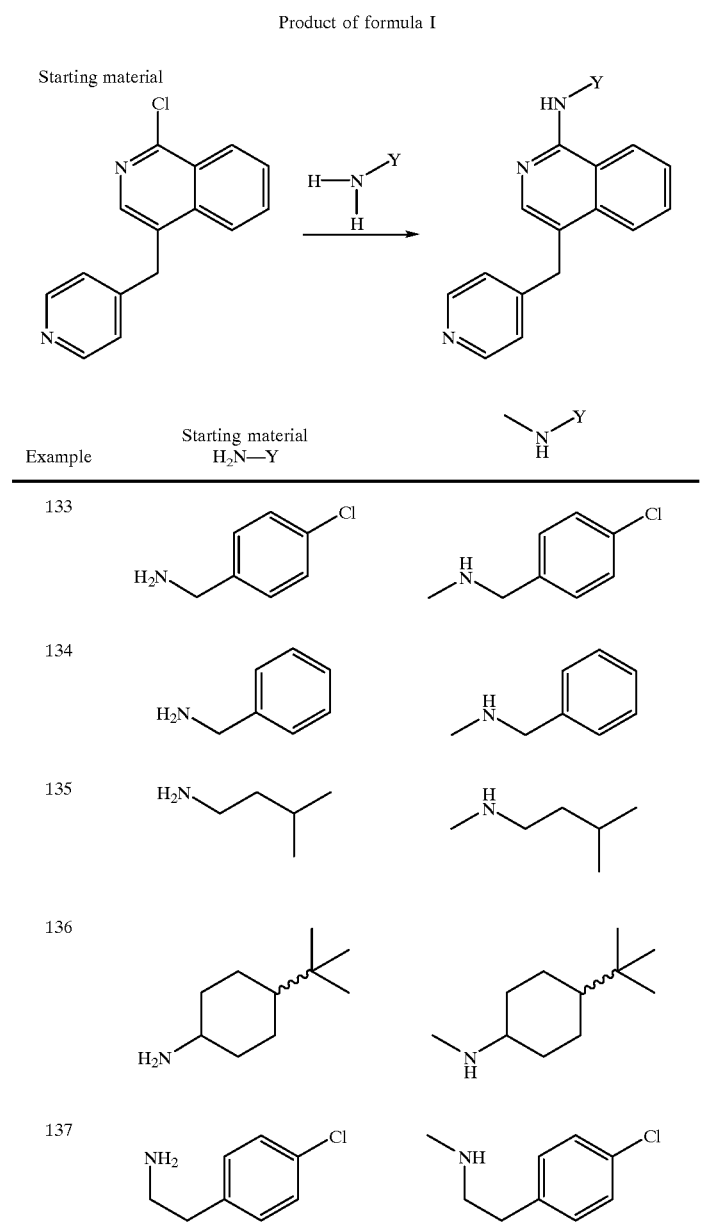

-continued

Product of formula I

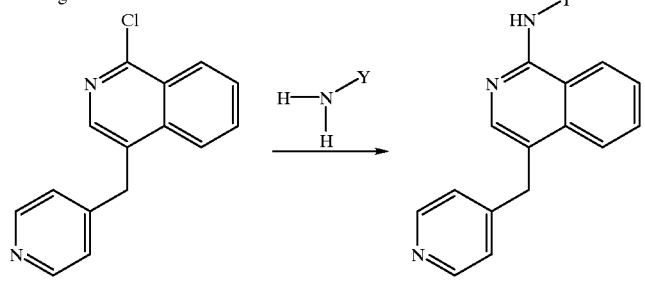

| Example | Starting material H₂N—Y |  |
|---|---|---|
| 138 | 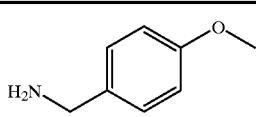 | 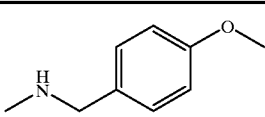 |
| 139 | 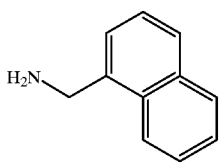 | 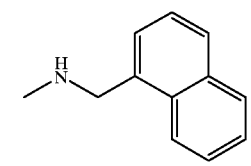 |
| 140 | 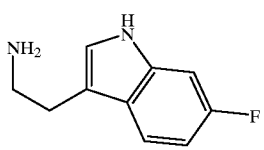 | 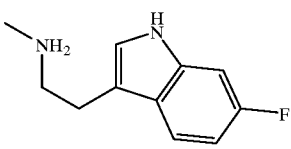 |

Example 141

Test for Activity Against Flt-1 VEGF Receptor Tyrosine Kinase Activity

The test is carried out using Flt-1 VEGF receptor tyrosine kinase, as described above. The IC$_{50}$ values obtained are shown below, insofar as they were calculated accurately:

| Title compound of Example | IC$_{50}$ ($\mu$M) |
|---|---|
| 1 | 0.802 |
| 2 | 0.346 |
| 3 | >1 |
| 4 | >1 |
| 5 | 0.344 |

Example 142

Soft Capsules 5000 soft gelatin capsules each comprising 0.05 g of one of the compounds of formula I mentioned in the preceding Examples as active ingredient are prepared as follows:
Composition:
active ingredient 250 g
Lauroglykol 2 liters Preparation method: The powdered active ingredient is suspended in Lauroglykol® (propylene glycol laurate, Gattefossé S.A., Saint Priest, France) and ground to a particle size of approximately from 1 to 3 $\mu$m in a wet pulverizer. 0.419 g portions of the mixture are then introduced into soft gelatin capsules by means of a capsule-filling machine.

What is claimed is:

1. A compound of formula I

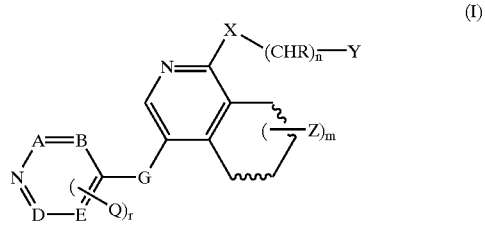

wherein
r is from 0 to 2;
n is from 0 to 2;
m is from 0 to 4;
A, B, D and E are each independently of the others N or CH, with the proviso that not more than two of those radicals are N;

G is lower alkylene, —CH₂—O—, —CH₂—S—, —CH₂—NH—, oxa (—O—), thia (—S—) or imino (—NH—), or is lower alkylene substituted by acyloxy or by hydroxy;

Q is lower alkyl;

R is H or lower alkyl;

X is imino, oxa or thia;

Y is lower alkyl, aryl, heteroaryl or unsubstituted or substituted cycloalkyl; and Z is amino, mono- or di-substituted amino, halogen, alkyl, substituted alkyl, hydroxy, etherified or esterified hydroxy, nitro, cyano, carboxy, esterified carboxy, alkanoyl, carbamoyl, N-mono- or N,N-di-substituted carbamoyl, amidino, guanidino, mercapto, sulfo, phenylthio, phenyl-lower alkythio, alkylphenylthio, phenylsulfinyl, phenyl-lower alkylsulfinyl, alkyiphenylsulfinyl, phenylsulfonyl, phenyl-lower alkanesulfonyl or alkylphenylsulfonyl, and where, if more than one radical Z is present (m≧2), the substituents Z are identical or different;

and wherein the bonds indicated by a wavy line are either single bonds or double bonds;

or an N-oxide of the mentioned compound, wherein one or more N atoms carry an oxygen atom;

or a salt thereof.

2. A compound of formula I according to claim 1, wherein r is from 0 to 2;

n is from 0 to 2;

m is from 0 to 4;

A, B, D and E are each independently of the others N or CH, with the proviso that not more than two of those radicals are N;

G is lower alkylene, lower alkylene substituted by acyloxy or by hydroxy, —CH₂—O—, —CH₂—S—, —CH₂—NH—, oxa (—O—), thia (—S—) or imino (—NH—);

Q is lower alkyl;

R is H or lower alkyl;

X is imino, oxa or thia;

Y is aryl, heteroaryl or unsubstituted or substituted cycloalkyl; and

Z is amino, mono- or di-substituted amino, halogen, alkyl, substituted alkyl, hydroxy, etherified or esterified hydroxy, nitro, cyano, carboxy, esterified carboxy, alkanoyl, carbamoyl, N-mono- or N,N-di-substituted carbamoyl, amidino, guanidino, mercapto, sulfo, phenylthio, phenyl-lower alkylthio, alkylphenylthio, phenylsulfinyl, phenyl-lower alkylsulfinyl, alkylphenylsulfinyl, phenylsulfonyl, phenyl-lower alkanesulfonyl or alkylphenylsulfonyl, and where, if more than one radical Z is present (m≧2), the substituents Z are identical or different;

and wherein the bonds indicated by a wavy line are either single bonds or double bonds;

or an N-oxide of the mentioned compound, wherein one or more N atoms carry an oxygen atom;

or a salt thereof.

3. A compound of formula I according to claim 1, wherein r is from 0 to 2;

n is 0 or 1;

m is 0, or is 1;

A, B, D and E are each CH, or A, D and E are each CH and B is N;

G is lower alkylene, —CH₂—NH—, —CH₂—O—, hydroxymethylene or benzoyloxy-methylene;

Q is methyl which is bonded to A, to D or to A and D;

R is H or lower alkyl;

X is imino, oxa or thia;

Y is phenyl that is unsubstituted or substituted by one or two identical or different substituents selected from the group consisting of amino; lower alkanoylamino, halogen, lower alkyl, halo-lower alkyl, lower alkoxy, phenyl-lower alkoxy, cyano, lower alkenyl, $C_8$–$C_{12}$alkoxy, lower alkoxycarbonyl, carbamoyl, lower alkylcarbamoyl, lower alkanoyl, phenyloxy, halo-lower alkyloxy, lower alkoxycarbonyl, lower alkylmercapto, halo-lower alkylmercapto, hydroxy-lower alkyl, lower alkanesulfonyl, halo-lower alkanesulfonyl, phenylsulfonyl, dihydroxybora, 2-methyl-pyrimidin-4-yl, oxazol-5-yl, 2-methyl-1,3-dioxolan-2-yl, 1H-pyrazol-3-yl, 1-methyl-pyrazol-3-yl, and lower alkylenedioxy bonded to two adjacent carbon atoms;

Z is amino; N-lower alkylamino; hydroxy-lower alkylamino; phenyl-lower alkylamino; N,N-di-lower alkylamino; N-phenyl-lower alkyl-N-lower alkylamino; N,N-di-lower alkylphenylamino; lower alkanoylamino or a substitutent selected from the group consisting of benzoylamino and phenyl-lower alkoxycarbonylamino, wherein the phenyl radical in each case is unsubstituted or substituted by nitro, halogen, amino, N-lower alkylamino, N,N-di-lower alkylamino, hydroxy, cyano, carboxy, lower alkoxycarbonyl, lower alkanoyl or by carbamoyl; or Z is halogen; and the bonds indicated by a wavy line are both a double bond, or are both a single bond;

or a salt thereof.

4. A compound of formula I according to claim 1, wherein r is 0;

n is 0;

m is 0;

A, B, D and E are each CH;

G is lower alkylene;

X is imino;

Y is phenyl that is unsubstituted or substituted by one or two identical or different substituents selected from the group consisting of halogen; lower alkyl; and halo-lower alkyl; and the bonds indicated by a wavy line are double bonds;

or a salt thereof.

5. A compound of formula I according to claim 1, wherein r is 0;

n is from 0 to 2;

m is 0;

A, B, D and E are each CH;

G is methylene;

R is H;

X is imino; and

Y is phenyl that is unsubstituted or substituted by halogen or by lower alkoxy; naphthyl; cyclohexyl that is unsubstituted or substituted by lower alkyl; or indolyl that is unsubstituted or substituted by halogen; especially 6-fluoroindol-3-yl; or is lower alkyl;

or a salt thereof where a salt-forming group is present.

6. A compound according to claim 1 which is 1-(3,5-dimethylanilino)-4-(pyridin-4ylmethyl)-isoquinoline, or a pharmaceutically acceptable salt thereof.

7. A compound according to claim 1 of the formula

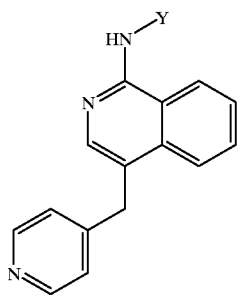

which falls within the scope of formula I, selected from the group of compounds of that formula wherein Y is one of the radicals shown below:

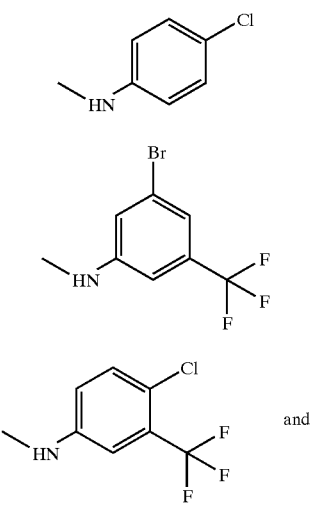

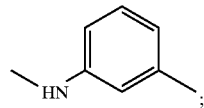

or in each case a salt thereof.

8. A method of treating a disease responsive to inhibition of VEGF receptor tyrosine kinase or to inhibition of angiogenesis, wherein a compound of formula I or an N-oxide thereof, or a pharmaceutically acceptable salt thereof, according to claim 1 is administered in an amount that is effective against the mentioned disease to a warm-blooded animal requiring such treatment.

9. A pharmaceutical composition which is suitable for administration to a warm-blooded animal suffering from a disease responsive to inhibition of angiogenesis or of VEGF receptor tyrosine kinase, comprising a compound of formula I or an N-oxide thereof, or a pharmaceutically acceptable salt thereof, according to claim 1 in an amount that is effective in inhibiting angiogenesis or VEGF receptor tyrosine kinase, together with at least one pharmaceutically acceptable carrier.

10. A compound according to claim 1 which is 1-(4-t-butylanilino)-4-(pyridin-4ylmethyl)-isoquinoline, or a pharmaceutically acceptable salt thereof.

11. A compound according to claim 1 which is (1-(4-isopropyl-3-methylanilino)-4-(pyridin-4ylmethyl)-isoquinoline, or a pharmaceutically acceptable salt thereof.

12. A pharmaceutical composition comprising at least one pharmaceutically acceptable carrier and a therapeutically effective amount of a compound of formula I according to claim 1, or a pharmaceutically acceptable salt thereof.

* * * * *